(12) United States Patent
Adamis et al.

(10) Patent No.: US 7,563,255 B2
(45) Date of Patent: Jul. 21, 2009

(54) IMPLANTABLE DRUG DELIVERY DEVICE AND USE THEREOF

(75) Inventors: Anthony P. Adamis, Jamaica Plain, MA (US); Joan W. Miller, Winchester, MA (US); Evangelos S. Gragoudas, Lexington, MA (US); Mark J. Mescher, West Newton, MA (US); Christopher E. Dubé, Lexington, MA (US); Jeffrey T. Borenstein, Hilliston, MA (US); Marcie G. Weinstein, Pittsburgh, PA (US); Raanan A. Miller, Chestnut Hill, MA (US); Mitchell L. Hansberry, Southborough, MA (US)

(73) Assignees: Massachusetts Eye and Ear Infirmary, Boston, MA (US); The Charles Stark Draper Laboratory Inc., Cambridge, MA (US)

( * ) Notice: Subject to any disclaimer, the term of this patent is extended or adjusted under 35 U.S.C. 154(b) by 1006 days.

(21) Appl. No.: 10/139,656

(22) Filed: May 2, 2002

(65) Prior Publication Data

US 2003/0069560 A1   Apr. 10, 2003

Related U.S. Application Data

(60) Provisional application No. 60/288,373, filed on May 3, 2001, provisional application No. 60/291,340, filed on May 16, 2001, provisional application No. 60/291,445, filed on May 16, 2001, provisional application No. 60/332,199, filed on Nov. 21, 2001, provisional application No. 60/332,200, filed on Nov. 21, 2001, provisional application No. 60/334,177, filed on Nov. 29, 2001.

(51) Int. Cl.
*A61M 35/00* (2006.01)

(52) U.S. Cl. .................. 604/294; 604/89; 604/132; 604/891.1

(58) Field of Classification Search .................. 604/89, 604/132, 294, 891.1
See application file for complete search history.

(56) References Cited

U.S. PATENT DOCUMENTS 3,416,530 A   12/1968   Ness ........................ 128/260

(Continued)

FOREIGN PATENT DOCUMENTS

JP   01-285274   11/1989

(Continued)

OTHER PUBLICATIONS

Bae et al., "Pulsatile Drug Release by Electric Stimulus," *ACS Symposium Series: Polymeric Drugs and Drug Administration*, pp. 98-110 (1994).

(Continued)

*Primary Examiner*—Nicholas D Lucchesi
*Assistant Examiner*—Laura A Bouchelle
(74) *Attorney, Agent, or Firm*—Goodwin Procter LLP

(57) ABSTRACT

The invention provides a miniaturized, implantable drug delivery device and a method of delivering over a prolonged period of time one or more drugs using such a device. The drug delivery device can be adapted for attachment to the outer surface of an eye. Once attached to the outer surface of an eye, the device can deliver one or more drugs directly into the eye for preventing or ameliorating the symptoms of a particular ocular disorder.

63 Claims, 13 Drawing Sheets

U.S. PATENT DOCUMENTS

| | | | |
|---|---|---|---|
| 3,618,604 A | 11/1971 | Ness et al. | 128/260 |
| 3,692,027 A | 9/1972 | Ellinwood, Jr. | |
| 3,828,777 A | 8/1974 | Ness | 128/260 |
| 3,923,060 A | 12/1975 | Ellinwood, Jr. | |
| 3,961,628 A | 6/1976 | Arnold | 128/260 |
| 3,963,025 A | 6/1976 | Whitaker et al. | |
| 4,003,379 A | 1/1977 | Ellinwood, Jr. | 128/260 |
| 4,014,335 A | 3/1977 | Arnold | 128/260 |
| 4,146,029 A | 3/1979 | Ellinwood, Jr. | 128/260 |
| 4,177,256 A | 12/1979 | Michaels et al. | 424/22 |
| 4,180,073 A | 12/1979 | Michaels | 128/260 |
| 4,186,184 A | 1/1980 | Zaffaroni | 424/14 |
| 4,203,442 A | 5/1980 | Michaels | 128/260 |
| 4,281,654 A | 8/1981 | Shell et al. | 128/260 |
| 4,300,557 A | 11/1981 | Refojo et al. | 128/260 |
| 4,327,725 A | 5/1982 | Cortese et al. | 128/260 |
| 4,360,019 A | 11/1982 | Portner et al. | 128/213 R |
| 4,475,916 A | 10/1984 | Himmelstein | 604/890 |
| 4,507,115 A | 3/1985 | Kambara et al. | |
| 4,544,371 A | 10/1985 | Dormandy, Jr. et al. | 604/891 |
| 4,585,652 A | 4/1986 | Miller et al. | |
| 4,731,049 A | 3/1988 | Parsi | |
| 4,731,051 A | 3/1988 | Fischell | |
| 4,734,092 A | 3/1988 | Millerd | 604/67 |
| 4,793,825 A | 12/1988 | Benjamin et al. | |
| 4,853,224 A | 8/1989 | Wong | 424/427 |
| 4,946,450 A | 8/1990 | Erwin | |
| 4,957,494 A | 9/1990 | Wong et al. | 604/892.1 |
| 4,959,217 A | 9/1990 | Sanders et al. | 424/473 |
| 4,994,023 A | 2/1991 | Wellinghoff et al. | |
| 4,997,652 A | 3/1991 | Wong | 424/428 |
| 5,041,107 A | 8/1991 | Heil, Jr. | |
| 5,061,242 A | 10/1991 | Sampson | 604/118 |
| 5,147,647 A | 9/1992 | Darougar | 424/427 |
| 5,164,188 A | 11/1992 | Wong | 424/428 |
| 5,167,625 A | 12/1992 | Jacobsen et al. | |
| 5,170,801 A | 12/1992 | Casper et al. | |
| 5,178,635 A | 1/1993 | Gwon et al. | 623/4 |
| 5,196,002 A | 3/1993 | Hanover et al. | |
| 5,207,217 A * | 5/1993 | Cocozza et al. | 128/203.21 |
| 5,236,689 A | 8/1993 | Wong et al. | 424/473 |
| 5,254,081 A | 10/1993 | Maurer et al. | |
| 5,266,332 A | 11/1993 | Dong et al. | 424/473 |
| 5,279,607 A | 1/1994 | Schentag et al. | |
| 5,300,114 A | 4/1994 | Gwon et al. | 623/4 |
| 5,318,557 A | 6/1994 | Gross | |
| 5,322,691 A | 6/1994 | Darougar et al. | 424/427 |
| 5,336,213 A * | 8/1994 | D'Angelo et al. | 604/890.1 |
| 5,348,746 A | 9/1994 | Dong et al. | 424/473 |
| 5,366,454 A | 11/1994 | Currie et al. | |
| 5,368,588 A | 11/1994 | Bettinger | |
| 5,368,704 A | 11/1994 | Madou et al. | |
| 5,378,475 A | 1/1995 | Smith et al. | 424/473 |
| 5,387,419 A | 2/1995 | Levy et al. | |
| 5,391,381 A | 2/1995 | Wong et al. | 424/473 |
| 5,393,533 A | 2/1995 | Versic | |
| 5,403,901 A | 4/1995 | Namdaran et al. | |
| 5,409,457 A | 4/1995 | del Cerro et al. | 604/51 |
| 5,415,162 A | 5/1995 | Casper et al. | |
| 5,443,505 A | 8/1995 | Wong et al. | 623/4 |
| 5,443,508 A | 8/1995 | Giampapa | |
| 5,445,616 A | 8/1995 | Kratoska et al. | 604/141 |
| 5,466,233 A | 11/1995 | Weiner et al. | 604/890.1 |
| 5,466,466 A | 11/1995 | Müller et al. | 424/449 |
| 5,475,096 A | 12/1995 | Gold et al. | 536/23.1 |
| 5,476,511 A | 12/1995 | Gwon et al. | 623/4 |
| 5,490,962 A | 2/1996 | Cima et al. | |
| 5,516,522 A | 5/1996 | Peyman et al. | 424/426 |
| 5,518,680 A | 5/1996 | Cima et al. | |
| 5,582,981 A | 12/1996 | Toole et al. | 435/6 |
| 5,607,418 A | 3/1997 | Arzbaecher | 604/891.1 |
| 5,632,984 A | 5/1997 | Wong et al. | 424/85.4 |
| 5,660,846 A | 8/1997 | Cheikh | 424/423 |
| 5,679,666 A | 10/1997 | Clark | |
| 5,700,286 A | 12/1997 | Tartaglia et al. | |
| 5,707,385 A | 1/1998 | Williams | |
| 5,707,643 A | 1/1998 | Ogura et al. | 424/428 |
| 5,710,165 A | 1/1998 | Kapin et al. | |
| 5,725,493 A * | 3/1998 | Avery et al. | 604/9 |
| 5,736,152 A | 4/1998 | Dunn | 424/426 |
| 5,743,274 A | 4/1998 | Peyman | |
| 5,756,291 A | 5/1998 | Griffin et al. | 435/6 |
| 5,766,242 A | 6/1998 | Wong et al. | 623/4 |
| 5,766,619 A | 6/1998 | Aiache et al. | |
| 5,770,592 A | 6/1998 | Clark | 514/179 |
| 5,773,019 A | 6/1998 | Ashton et al. | 424/423 |
| 5,794,613 A | 8/1998 | Piskorski | |
| 5,797,898 A | 8/1998 | Santini, Jr. et al. | 604/890.1 |
| 5,824,072 A | 10/1998 | Wong | 623/4 |
| 5,824,073 A | 10/1998 | Peyman | |
| 5,830,173 A | 11/1998 | Avery et al. | 604/9 |
| 5,836,935 A | 11/1998 | Ashton et al. | 604/891.1 |
| 5,840,867 A | 11/1998 | Toole et al. | 536/23.1 |
| 5,869,078 A | 2/1999 | Baudino | 424/423 |
| 5,869,079 A | 2/1999 | Wong et al. | 424/426 |
| 5,888,533 A | 3/1999 | Dunn | 424/423 |
| 5,897,878 A | 4/1999 | Dong et al. | 424/473 |
| 5,902,598 A | 5/1999 | Chen et al. | 424/423 |
| 5,904,144 A | 5/1999 | Hammang et al. | 128/898 |
| 5,916,584 A | 6/1999 | O'Donoghue et al. | 424/426 |
| 5,993,414 A | 11/1999 | Haller | 604/93 |
| 6,001,386 A | 12/1999 | Ashton et al. | 424/423 |
| 6,010,492 A * | 1/2000 | Jacobsen et al. | 604/503 |
| 6,056,734 A | 5/2000 | Jacobsen et al. | 604/891.1 |
| 6,074,661 A | 6/2000 | Olejnik et al. | |
| 6,074,673 A | 6/2000 | Guillen | 424/501 |
| 6,110,485 A | 8/2000 | Olejnik et al. | 424/428 |
| 6,120,789 A | 9/2000 | Dunn | 424/426 |
| 6,123,861 A | 9/2000 | Santini, Jr. et al. | 216/2 |
| 6,126,687 A | 10/2000 | Peyman | |
| 6,146,366 A | 11/2000 | Schachar | |
| 6,165,155 A | 12/2000 | Jacobsen et al. | 604/156 |
| 6,203,523 B1 | 3/2001 | Haller et al. | 604/93.01 |
| 6,217,896 B1 | 4/2001 | Benjamin | 424/427 |
| 6,251,090 B1 | 6/2001 | Avery et al. | 604/9 |
| 6,277,401 B1 | 8/2001 | Bello et al. | 424/449 |
| 6,283,949 B1 | 9/2001 | Roorda | 604/288.02 |
| 6,283,951 B1 | 9/2001 | Flaherty et al. | 604/529 |
| 6,299,895 B1 | 10/2001 | Hammang et al. | 424/427 |
| 6,306,420 B1 | 10/2001 | Cheikh | 424/422 |
| 6,312,393 B1 | 11/2001 | Abreu | 600/558 |
| 6,317,630 B1 | 11/2001 | Gross et al. | 604/20 |
| 6,319,245 B1 | 11/2001 | Berrigan | 604/891.1 |
| 6,331,313 B1 | 12/2001 | Wong et al. | 424/427 |
| 6,349,232 B1 | 2/2002 | Gordon | |
| 6,364,865 B1 | 4/2002 | Lavi et al. | 604/411 |
| 6,368,626 B1 | 4/2002 | Bhatt et al. | 424/473 |
| 6,368,629 B1 | 4/2002 | Watanabe et al. | 424/482 |
| 6,369,116 B1 | 4/2002 | Wong et al. | 514/913 |
| 6,375,972 B1 | 4/2002 | Guo et al. | 424/423 |
| 6,413,540 B1 | 7/2002 | Yaacobi | 424/427 |
| 6,415,790 B1 | 7/2002 | Leedom et al. | |
| 6,416,777 B1 | 7/2002 | Yaacobi | 424/428 |
| 6,491,666 B1 | 12/2002 | Santini, Jr. et al. | |
| 6,506,437 B1 | 1/2003 | Harish et al. | |
| 6,527,762 B1 | 3/2003 | Santini, Jr. et al. | |
| 6,537,256 B2 | 3/2003 | Santini, Jr. et al. | |
| 6,551,838 B2 | 4/2003 | Santini, Jr. et al. | |
| 6,656,162 B2 | 12/2003 | Santini, Jr. et al. | |
| 6,756,049 B2 | 6/2004 | Brubaker et al. | |
| 2002/0026176 A1 | 2/2002 | Varner et al. | 604/891.1 |
| 2002/0072784 A1 | 6/2002 | Sheppard, Jr. et al. | |
| 2002/0086051 A1 | 7/2002 | Viscasillas | 424/451 |
| 2002/0099359 A1 | 7/2002 | Santini, Jr. et al. | |

| | | |
|---|---|---|
| 2002/0107470 A1 | 8/2002 | Richards et al. |
| 2002/0111601 A1 | 8/2002 | Thompson |
| 2002/0138067 A1 | 9/2002 | Sheppard, Jr. et al. |
| 2002/0151776 A1 | 10/2002 | Shawgo et al. |
| 2002/0173745 A1 | 11/2002 | Santini, Jr. et al. |
| 2002/0183721 A1 | 12/2002 | Santini, Jr. et al. |
| 2002/0187260 A1 | 12/2002 | Sheppard, Jr. et al. |
| 2003/0010808 A1 | 1/2003 | Uhland et al. |
| 2003/0036746 A1 | 2/2003 | Penner et al. |
| 2003/0049865 A1 | 3/2003 | Santini, Jr. et al. |
| 2003/0065377 A1 | 4/2003 | Davila et al. |
| 2003/0077837 A1 | 4/2003 | Tupper et al. |
| 2003/0088307 A1 | 5/2003 | Shulze et al. |
| 2003/0100860 A1 | 5/2003 | Jones et al. |
| 2003/0100865 A1 | 5/2003 | Santini, Jr. et al. |
| 2003/0104590 A1 | 6/2003 | Santini, Jr. et al. |
| 2003/0105455 A1 | 6/2003 | Santini, Jr. et al. |
| 2003/0175324 A1 | 9/2003 | Robinson et al. |
| 2004/0015154 A1 | 1/2004 | Harper et al. |
| 2004/0020173 A1 | 2/2004 | Cho |
| 2004/0024382 A1 | 2/2004 | Cho et al. |
| 2004/0030380 A1 | 2/2004 | Shulze et al. |

FOREIGN PATENT DOCUMENTS

| | | |
|---|---|---|
| JP | 7-505060 | 6/1995 |
| JP | 2003-513755 | 4/2003 |
| WO | 86/00519 A | 1/1986 |
| WO | WO 86/00519 | 1/1986 |
| WO | 91/16869 | 11/1991 |
| WO | WO-93/09829 | 5/1993 |
| WO | 93/21874 | 11/1993 |
| WO | 94/05257 | 3/1994 |
| WO | 94/13305 | 6/1994 |
| WO | 94/21314 A | 9/1994 |
| WO | 00/38714 | 7/2000 |
| WO | 00/40089 A | 7/2000 |
| WO | 01/28472 A1 | 4/2001 |
| WO | 01/28474 A1 | 4/2001 |
| WO | 01/30323 | 5/2001 |
| WO | WO-01/35928 | 5/2001 |
| WO | 01/80825 A | 11/2001 |
| WO | WO-03/020172 | 3/2003 |

OTHER PUBLICATIONS

Bates et al., "New Amorphous Thin-Film Lithium Electrolyte and Rechargeable Microbattery," *IEEE 35th International Power Sources Symposium*, pp. 337-339 (1992).

Jones et al., "Development and Performance of a Rechargeable Thin-Film Solid-State Microbattery," *Journal of Power Sources*, vol. 54, pp. 63-67 (1995).

Kwon et al., "Electrically Erodible Polymer Gel for Controlled Release of Drugs," *Nature*, vol. 354, pp. 291-293 (Nov. 1991).

Tierney et al., "Electroreleasing Composite Membranes for Delivery of Insulin and Other Biomacromolecules," *Journal of the Electrochemical Society*, vol. 137, No. 6, pp. 2005-2006 (Jun. 1990).

Adamis et al. "Increased Vascular Endothelial Growth Factor Levels in the Vitreous of Eyes with Proliferative Diabetic Retinopathy" *Am. J. Ophthalmol.* (1994) 118:445-450.

Adamis et al, "Inhibition of Vascular Endothelial Growth Factor Prevents Retinal Ischemia-Associated Iris Neovascularization in a Nonhuman Primate" *Arch. Ophthalmol.* (1996) 114:66-71.

Aiello et al. "Vascular Endothelial Growth Factor in Ocular Fluid of Patients with Diabetic Retinopathy and Other Retinal Disorders" *N. Engl. J. Med.* (1994) 331:1480-1487.

Aiello et al. "Suppression of Retinal Neovascularization In Vivo by Inhibition of Vascular Endothelial Growth Factor (VEGF) Using Soluble VEGF-receptor Chimeric Proteins" *Proc. Natl. Acad. Sci. USA* (1995) 92:10457-10461.

Amano et al. "Requirement for Vascular Endothelial Growth Factor in Wound-and-Inflammation-Related Corneal Neovascularization" *Invest. Ophthalmol. Vis. Sci.* (1998) 39:18-22.

Ambati et al. "Diffusion of High Molecular Weight Compounds Through Sclera" *Invest. Ophthalmol. Vis. Sci.* (2000) 41:1181-1185.

Ambati et al. "Elevated γ-Aminobutyric Acid, Glutamate, and Vascular Endothelial Growth Factor Levels in the Vitreous of Patients with Proliferative Diabetic Retinopathy" *Arch. Ophthalmol.* (1997) 115:1161-1166.

Ambati et al. "Transscleral Delivery of Antibodies to the Posterior Segment" *Invest. Ophthalmol. Vis. Sci.* (1999) 40:S86 Abstract 457-B417.

Ambati et al. "Transscleral Delivery of Bioactive Protein to the Choroid and Retina" *Invest. Ophthalmol. Vis. Sci.* (2000) 41:1186-1191.

Arroyo et al. "In Vivo Photoactivation of Caged-Thrombin" *Thromb. Haemost*, (1997) 78:791-793.

Asrani et al. "Feasibility of Laser-Targeted Photoocclusion of the Choriocapillary Layer in Rats" *Invest. Ophthalmol. Vis. Sci.* (1997) 38:2702-2710.

Barza et al. "Regional Differences in Ocular Concentration of Gentamicin After Subconjunctival and Retrobulbar Injection in the Rabbit" *Am. J. Ophthalmo*l. (1997) 83:407-413.

Barza et al. "Transscleral Iontophoresis of Cefazolin, Ticarcillin, and Gentamicin in the Rabbit" Ophthalmology (1986) 93:133-139.

Barza et al. "Intraocular Penetration of Gentamicin After Subconjunctival and Retrobulbar Injection" *Amer. J. Ophthalmol.* (1978) 85:541-547.

Baum et ál. "Preferred Routes of Antibiotic Administration in Treatment of Bacterial Ulcers of the Cornea" *Int. Ophthalmol. Clin.* (1973) 13:31-37.

Baum et al. "Treatment of Postcataract Bacterial Endophthalmitis with Periocular and Systemic Antibiotics and Corticosteriods" *Trans. Am. Acad. Ophthalmol. Otolaryngo.* (1976) 81:151-162.

Becker et al. "In Vivo Significance of ICAM-1-Dependent Leukocyte Adhesion in Early Corneal Angiogenesis" *Invest. Ophthalmol. Vis. Sci.* (1999) 40:612-618.

Bennett et al. "Photoreceptor Cell Rescue in Retinal Degeneration (*rd*) Mice by In Vivo Gene Therapy" *Nat. Med.* (1996) 2:649-654.

Bill "Movement of Albumin and Dextran Through the Sclera" *Arch. Ophthalmol.* (1965) 74:248-252.

Brown et al. "In Vivo and In Vitro Release of Macromolecules from Polymeric Drug Delivery Systems" *J. Pharm. Sci.* (1983) 72:1181-1185.

Burnette "Theory of Mass Transfer" *In: Controlled Drug Delivery*, $2^{nd}$ ed (1987) 29:95-138.

Canakis et al. "Characterization of Diffusion Across the Sclera Using FITC-Conjugates of Different Molecular Weights" *Invest. Ophthalmol. Vis. Sci.* (1997) Abstract 38: 683-B594.

Carrasquillo et al. "Controlled Delivery of Anti-VEGF Aptamer EYE001 with Poly(lactic-co-glycolic) Acid Microspheres" Poster presentation in 2002.

Cooper et al. "Transport Across Epithelial Membranes" *J. Controlled Release* (1987) 6:23-35.

DiPolo et al. "Prolonged Delivery of Brain-derived Neurotrophic Factor by Adenovirus-infected Müller Cells Temporarily Rescues Injured Retinal Ganglion Cells" *Proc. Natl. Acad. Sci. USA* (1998) 95:3978-3983.

Edelhauser et al. "Permeability of Human Cornea and Sclera to Sulfonamide Carbonic Anhydrase Inhibitors" *Arch. Ophthalmol.* (1988) 106:1110-1115.

Edwards et al. "Fiber Matrix Model of Sclera and Corneal Stroma for Drug Delivery to the Eye" *Am. Inst. Chem. Eng. J.* (1998) 44:214-225.

The Eyetech Study Group "Preclinical and Phase 1A Clinical Evaluation of an Anti-VEGF Pegylated Aptamer (EYE001) for the Treatment of Exudative Age-Related Macular Degeneration" *J. Retinal Vitreous Diseases* (2002) 22: 143-152.

Faktorovich et al. "Photoreceptor Degeneration in Inherited Retinal Dystrophy Delayed by Basic Fibroblast Growth Factor" *Nature* (1990) 347:83-86.

Fatt et al. "Flow of Water in the Sclera" *Exptl. Eye Res.* (1970) 10:243-249.

Friedmann "Overcoming the Obstacles to Gene Therapy" *Sci. Am.* (1997) 96-101.

Gautie et al. "Transscleral Coulomb Controlled Iontophoresis of Ganciclovir in Rabbits: Safety and Pharmacokinetics" *Invest. Ophthalmol. Vis. Sci.* (1997) Abstract 720-B631.

Husain et al. "Vascular Endothelial Growth Factor (VEGF) Expression is Correlated with Choroidal Neovascularization in a Monkey Model" *Invest. Ophthalmol. Vis. Sci.* (1997) 38:S501.

Hyndiuk et al. "Radioactive Depot-Corticosteroid Penetration into Monkey Ocular Tissue. I. Retrobulbar and Systemic Administration" *Arch. Ophthalmol.* (1968) 80:449-503.

Ishibashi et al. "Expression of Vascular Endothelial Growth Factor in Experimental Choroidal Neovascularization" *Arch. Clin. Exp. Ophthalmol.* (1997) 235:159-167.

Jellinek et al. "Inhibition of Receptor Binding by High-Affinity RNA Ligands to Vascular Endothelial Growth Factor" *Biochem.* (1994) 33:10450-10456.

Jo et al. "Fabrication of Three-Dimensional Microfluidic Systems by Stacking Molded Polydimethylsiloxane (PMDS) Layers" *SPIE* (1999) 3877: 222-229.

Kimura et al. "A New Vitreal Drug Delivery System Using an Implantable Biodegradable Polymeric Device" *Invest. Ophthalmol. Vis. Sci.* (1994) 35:2815-2819.

Kliffen et al. "Increased Expression of Angiogenic Growth Factors in Age-related Maculopathy" *Br. J. Ophthalmol.* (1997) 81:154-162.

Lam et al. "Transscleral Iontophoresis of Dexamethasone" *Arch. Ophthalmol.* (1989) 107:1368-1371.

Lam et al. "A Histopathologic Study of Retinal Lesions Inflicted by Transscleral Iontophoresis" *Graefe's. Arch. Clin. Exp. Ophthalmol.* (1991) 229:389-394.

Lang et al. "Ocular Drug Delivery Conventional Ocular Formulations" *Adv. Drug Delivery Rev.* (1995) 16:39-43.

Langer et al. "Polymers for the Sustained Release of Proteins and Other Macromolecules" *Nature* (1976) 263:797-800.

Lim et al. "Intraocular Tissue Plasminogen Activator Concentrations after Subconjunctival Delivery" *Ophthalmology* (1993) 100:373-376.

Lincoff et al. "Choroidal Concentration of Interferon After Retrobulbar Injection" *Invest. Ophthalmol. Vis. Sci.* (1996) 37:2768-2771.

Litwack et al. "Penetration of Gentamicin. Administered Intramuscularly and Subconjunctivally Into Aqueous Humor" *Arch. Ophthal.* (1969) 82:687-693.

Lopez et al. "Transdifferentiated Retinal Pigment Epithelial Cells Are Immunoreactive for Vascular Endothelial Growth Factor in Surgically Excised Age-Related Macular Degeneration-Related Choroidal Neovascular Membranes" *Invest. Ophthalmol. Vis. Sci.* (1996) 37:855-868.

Lu et al. "VEGF Increases Retinal Vascular ICAM-1 Expression In Vivo" *Invest. Ophthalmol. Vis. Sci.* (1999) 40:1808-1812.

Marmor et al. "Kinetics of Macromolecules Injected into the Subretinal Space" *Exp. Eye Res.* (1985) 40:687-696.

Maurice et al. "Diffusion Across the Sclera" *Exp. Eye Res.* (1977) 25:577-582.

Melder et al. "During Angiogenesis, Vascular Endothelial Growth Factor and Basic Fibroblast Growth Factor Regulate Natural Killer Cell Adhesion to Tumor Endothelium" *Nat. Med.* (1996) 2:992-997.

Miller et al. "Vascular Endothelial Growth Factor/Vascular Permeability Factor Is Temporally and Spatially Correlated with Ocular Angiogenesis in a Primate Model" *Am. J. Pathol.* (1994) 145:574-584.

Misono et al. "A Study of the Ability of Tissue Plasminogen Activator to Diffuse into the Subretinal Space After Intravitreal Injection in Rabbits" *Invest. Ophthalmol. Vis. Sci.* (1999) 40:S712.

Moritera et al. "Biodegradable Microspheres Containing Adriamycin in the Treatment of Proliferative Vitreoretinopathy" *Invest. Ophthalmol. Vis. Sci.* (1992) 33:3125-3130.

Moritera et al. "Microspheres of Biodegradable Polymers as a Drug-Delivery System in the Vitreous" *Invest. Ophthalmol. Vis. Sci.* (1991) 32:1785-1790.

Nilsson "The Uveoscleral Outflow Routes" *Eye* (1997) 11:149-154.

Okamoto et al. "Transgenic Mice with Increased Expression of Vascular Endothelial Growth Factor in the Retina: A New Model of Intraretinal and Subretinal Neovascularization" *Am. J. Pathol.* (1997) 151:281-291.

Olsen et al. "Human Sclera: Thickness and Surface Area" *Am. J. Ophthalmol.* (1998) 125:237-241.

Olsen et al. "Human Scleral Permeability: Effects of Age, Cryotherapy, Transscleral Diode Laser, and Surgical Thinning" *Invest. Ophthalmol. Vis. Sci.* (1995) 36:1893-1903.

Orkin et al. Report and Recommendations of the Panel to Assess the NIH Investment in Research on Gene Therapy (1995) 1-41.

Peyman et al. "Peroxidase Diffusion in the Normal and Laser-coagulated Primate Retina" *Invest. Ophthalmol.* (1972) 11:35-45.

Peyman et al. "Intravitreal Liposome-encapsulated Drugs: A Preliminary Human Report" *Int. Ophthalmol.* (1988) 12:175-182.

Rubsamen "Prevention of Experimental PVR with Intravitreal Sustained Release of 5-Fluorouracil" *Invest. Ophthalmol. Vis. Sci.* (1992) 33:728.

Ruckman et al. "2'-Fluoropyrimidine RNA-based Aptamers to the 165-Amino Acid Form of Vascular Endothelial Growth Factor ($VEGF_{165}$)" *J. Biol. Chem.* (1998) 273: 20556-20567.

Ryan "Subretinal Neovascularization: Natural History of an Experimental Model" *Arch. Ophthalmol.* (1982) 100:1804-1809.

Sakamoto et al. "Effect of Intravitreal Administration of Indomethacin on Experimental Subretinal Neovascularization in the Subhuman Primate" *Arch. Ophthalmol.* (1995) 113:222-226.

Sanborn et al. "Sustained-Release Ganciclovir Therapy for Treatment of Cytomegalovirus Retinitis. Use of an Intravitreal Device" *Arch. Ophthalmol.* (1992) 110:188-195.

Santini et al. "A Controlled-release Microchip" *Nature* (1999) 397:335-338.

Smith et al. "Intravitreal Sustained-Release Ganciclovir" *Arch. Ophthalmol.* (1992) 110:255-258.

Tolentino et al. "Vascular Endothelial Growth Factor Is Sufficient to Produce Iris Neovascularization and Neovascular Glaucoma in a Nonhuman Primate" *Arch. Ophthalmol.* (1996) 114:964-970.

Tremblay et al. "Reduced Toxicity of Liposome-Associated Amphotericin B Injected Intravitreally in Rabbits" *Invest. Ophthalmol. Vis. Sci.* (1985) 26:711-718.

Verma et al. "Gene Therapy—Promises, Problems and Prospects" *Nature* (1997) 389:239-242.

Vorwerk et al. "Chronic Low-Dose Glutamate Is Toxic to Retinal Ganglion Cells. Toxicity Blocked by Memantine" *Invest. Ophthalmol. Vis. Sci.* (1996) 37:1618-1624.

Weijtens et al. "Peribulbar Corticosteroid Injection: Vitreal and Serum Concentrations After Dexamethasone Disodium Phosphate Injection" *Am. J. Ophthalmol.* (1997) 123:358-363.

\* cited by examiner

IMPLANTABLE DRUG DELIVERY DEVICE AND USE THEREOF

RELATED APPLICATIONS

This application claims priority to and the benefit of U.S. Provisional Application Serial No. 60/288,373, filed May 3, 2001; U.S. Provisional Application Serial No. 60/291,340, filed May 16, 2001; U.S. Provisional Application Serial No. 60/291,445, filed May 16, 2001; U.S. Provisional Application Serial No. 60/332,199, filed Nov. 21, 2001; U.S. Provisional Application Serial No. 60/332,200, filed Nov. 21, 2001; and U.S. Provisional Application Serial No. 60/334,177, filed Nov. 29, 2001, the disclosures of each of which are incorporated by reference herein.

FIELD OF THE INVENTION

The invention relates generally to a drug delivery device and, more particularly, to a miniaturized, implantable drug delivery device.

BACKGROUND OF THE INVENTION

The way a particular drug is administered to a recipient can significantly affect the efficacy of the drug. For example, some therapies, in order to be optimal, require that the drug be administered locally to a particular target site. Furthermore, some of those drugs need to be present at the target site for a prolonged period of time to exert maximal effect.

One approach for achieving localized drug delivery involves the injection of drug directly into the site of desired drug activity. Unfortunately, this approach may require periodic injections of drug to maintain an effective drug concentration at the target site. In order to prolong the existence at the target site, the drug may be formulated into a slow release formulation (see, for example, Langer (1998) NATURE 392, Supp. 5-10). For example, the drug can be conjugated with polymers which, when administered to an individual, are then degraded, for example, by proteolytic enzymes or by hydrolysis, to gradually release drug into the target site. Similarly, drug can be trapped throughout insoluble matrices. Following administration, drug then is released via diffusion out of, or via erosion of the matrices. Alternatively, drug can be encapsulated within a semi-permeable membrane or liposome. Following administration, the drug is released either by diffusion through the membrane or via breakdown of the membrane. However, problems associated with localized drug injection can include, for example, repeated visits to a health care professional for repeated injections, difficulty in stabilizing drugs within slow release formulations, and the control of the concentration profile of the drug over time at the target site.

Another approach for localized drug delivery includes the insertion of a catheter to direct the drug to the desired target location. The drug can be pushed along the catheter from a drug reservoir to the target site via, for example, a pump or gravity feed. Typically, this approach employs an extracorporeal pump, an extracorporeal drug reservoir, or both an extracorporeal pump and extracorporeal drug reservoir. Disadvantages can include, for example, the risk of infection at the catheter's point of entry into the recipient's body, and that because of their size the pump and/or the reservoir may compromise the mobility and life style of the recipient.

Over the years, implantable drug delivery devices have been developed to address some of the disadvantages associated with localized injection of drug or the catheter-based procedures. A variety of implantable drug delivery devices have been developed to date.

One type of implantable drug delivery device includes the osmotically driven device. A variety of osmotic drug delivery devices are known in the art. For example, one such device is available commercially from Durect Corp. (Cupertino, Calif.) under the tradename DUROS®. Similarly another device is available from ALZA Scientific Products (Mountain View, Calif.), under the tradename ALZET®. In some devices, the influx of fluid into the device causes an osmotically active agent to swell. The swelling action can then be employed to push drug initially stored in a reservoir out of the device. DUROS® pumps reportedly deliver up to 200 mg of drug at rates as low as 0.5 μL per day. However, osmotic pumps stop working when the osmotic engine in the device or drug reservoir becomes exhausted. A variety of different osmotically driven drug delivery devices are described, for example, in U.S. Pat. Nos. 4,957,494, 5,236,689 and 5,391,381.

In addition to osmotically driven drug delivery devices, a variety of mechanical and electrochemical devices have been developed to date. U.S. Pat. No. 3,692,027 describes an implantable, electromechanical drug delivery device. The device includes, within a fluid impermeable and sealed casing, a watch-type drive mechanism that drives a circular wheel. The wheel contains a plurality of cavities, all of which apparently are radially disposed in a single diametral plane about the circumference of the wheel. Once the drug-containing cavity moves into alignment with an aperture through the casing, a piston associated with the cavity ejects medicine out of the cavity and through the aperture. This type of device can be quite large in size and, therefore, may be unsuitable for implantation into small cavities within the body.

U.S. Pat. No. 6,283,949 B1 discloses an implantable drug delivery device that includes a reservoir, a dispensing chamber adjacent to the reservoir, a dispensing passage provided along an interior surface of the dispensing chamber, and an actuator for applying a moving compressive force onto the dispensing passage. As a compressive force applied by the actuator moves along the dispensing passage, drug is simultaneously ejected out of the dispensing passage into a catheter for delivery to the target site, and additional drug is drawn into the dispensing passage from the reservoir. The size of this type of device may limit its applicability when implantation into a small body cavity is desired.

U.S. Pat. Nos. 5,797,898 and 6,123,861 disclose microchip based drug delivery devices. A plurality of drug reservoirs are etched into a substrate, for example, a single microchip. Drugs then are sealed within each of the reservoirs with a seal. The seal can be either a material that degrades over time or a material that dissolves upon application of an electric potential. See also Santini et al. (1999) NATURE 397: 335-338, which similarly discloses a solid-state silicon microchip that provides controlled release of a drug of interest via electrochemical dissolution of a thin membrane covering a micro-reservoir filled with drug.

However, there is still an ongoing need in the art for reliable, miniaturized, implantable drug delivery devices that permit the localized delivery of a drug of interest over a prolonged period of time.

SUMMARY OF THE INVENTION

The invention provides a miniaturized, implantable drug delivery device for delivering, over a prolonged period of time, a drug of interest to a preselected locus in a recipient, for example, a mammal, more preferably, a human. The device is miniaturized and thus can be implanted into a small body cavity. In one application, the device can be attached to the surface of an eye for delivering a drug into the eye. When attached, the device does not affect or otherwise restrict movement of the eye.

In one aspect, the implantable drug delivery device comprises: (a) a casing defining (i) an inner volume and (ii) an aperture port passing therethrough, wherein the inner volume is in fluid flow communication with the outside of the casing; (b) a reservoir member, for example, a drum or flexible support member, disposed within the casing, wherein the reservoir member defines a cavity for receiving the drug; and (c) a seal attached to the reservoir member for sealing drug within the cavity. The device optionally may also include a puncturing member for breaking the seal to permit drug disposed within the cavity to be released into the inner volume and to exit the casing via the aperture port.

In another aspect, the implantable drug delivery device comprises (a) a casing defining an aperture port passing therethrough; (b) a rotatable drum-type reservoir member disposed within the casing and having a surface defining a plurality of cavities for receiving the drug radially disposed about the drum, wherein all the cavities do not lie in a single diametral plane; and (c) a seal attached to the drum for sealing drug within at least one cavity, which when punctured permits drug disposed within a cavity to exit the casing via the aperture port.

The reservoir member can be a rigid member or a flexible support member. In a preferred embodiment, the reservoir member is a drum or cylinder. The cavities are defined by an outer surface of the drum or cylinder, or alternatively are defined by a compliant material disposed about the outer surface of the drum or cylinder. The cavities can be arranged in a square, rectangular or helical array about the surface of the reservoir member.

The cavities of the reservoir member, after being filled with drug (in solid, liquid, or gel form) are sealed. The seal can be fabricated from a fluid degradable material, such that upon contact with a fluid, the seal solubilizes or otherwise breaks down to release the drug disposed within the cavity. Alternatively, the seal can be fabricated from a fluid-insoluble material. As a result, the device further comprises a puncturing member, for example, a mechanical or electrochemical mechanism, for breaking or puncturing the seal to release the drug. Preferred mechanical puncturing members can be fixed or moveable (for example, via rotation and/or translation) relative to the casing and/or the reservoir member. The puncturing member optionally may further comprise one or more cutting or piercing instruments. Preferred electrochemical mechanisms include seal materials fabricated from, for example, a metal, preferably, gold, that dissolve upon application of an electrical potential across the seal. Upon dissolution, the contents of the cavity are released.

In one embodiment, the device comprises a drive mechanism, for example, a magnetic drive, for moving the puncturing member, the reservoir member, or both the puncturing member and the reservoir member. The drive mechanism can be used to bring the puncturing member into contact with a cavity seal for breaking the seal.

The device of the invention can be used to administer one or more drugs to a preselected locus in a mammal. In one embodiment, one drug is loaded into the cavities. In another embodiment, two or more different drugs are loaded into the same cavity for simultaneous release. In another embodiment, one drug is loaded into one cavity and a different drug is loaded into a second, different cavity. The latter procedure permits different drugs to be released into a target location at different times.

In a preferred embodiment, the casing has an outer surface complementary in shape to a surface of a preselected tissue, for example, an eye. In one aspect, the invention provides a drug delivery device comprising: (a) a casing defining an aperture port passing therethrough and having an exterior surface complementary in shape to an outer surface of an eye; (b) a reservoir member disposed within the casing, wherein the reservoir member defines a cavity for receiving the drug; and (c) a seal attached to the reservoir member for sealing the cavity, which when broken permits drug disposed within the cavity to exit the casing through the aperture port. The device can be used to administer a drug or a plurality of drugs to the surface of an eyeball. The drug can then pass through the sclera and into the inner portion of the eye to exert its effect.

In another aspect, the devices of the invention can be used to administer a drug to the tissue of interest. The method comprises the steps of: (a) attaching the implantable drug delivery device of the invention to a preselected locus, for example, the outer surface of the eye; and (b) permitting drug disposed within the cavity to be released from the cavity and exit the casing through the aperture port. In a preferred embodiment, in step (a), the implantable drug delivery device is fixed, for example, via a suture, a tissue adhesive, or a combination thereof, to tissue in the locus, for example, the outer surface of the eye.

BRIEF DESCRIPTION OF THE DRAWINGS

The foregoing and other aspects of the invention and the various features thereof may be more fully understood from the following description when read together with the accompanying drawings, in which:

FIG. 1A depicts an embodiment of the invention where a drug-containing reservoir member is coupled to a drive mechanism, FIG. 1B depicts an embodiment of the invention where a puncturing member is coupled to a drive mechanism, and FIG. 1C depicts an embodiment of the invention where both the reservoir member and the puncturing member are both coupled to different drive mechanisms (alternatively, both members can be coupled to the same drive mechanism).

FIG. 4A is a perspective view of such a device, and FIG. 4B is a perspective view of such a device depicting a magnetic drive/ratchet-type drive mechanism that drives both the rotatable puncturing member and the reservoir member.

FIG. 8A depicts a drum-type reservoir member in which cavities have been drilled into the surface of the drum, and FIG. 8B depicts a planar sheet of compliant material defining cavities that can be wrapped around a drum-type reservoir member.

In the drawings, which are not drawn to scale, like characters refer to the same or similar parts throughout the Figures.

DETAILED DESCRIPTION OF THE INVENTION

The invention provides a miniaturized, implantable drug delivery device capable of delivering one or more drugs at defined rates to a particular target location over a prolonged period of time. The devices of the invention can be used to deliver a drug of interest into a recipient, for example, a mammal, more specifically, a human. In view of its small size, it is contemplated that the drug delivery device may be implanted using minimally invasive procedures into a small body cavity, for example, an area adjacent to an organ, for example, a heart, an area adjacent to or within brain tissue, adjacent to or in a joint, or an eye socket, which when implanted delivers one or more drugs over a prolonged period of time to tissue or body fluid surrounding the implanted device. In one embodiment, the drug delivery device is adapted for attachment to an outer surface of an eye. When attached, the device delivers drug to the surface of the eye, which then passes through the sclera and into the target tissue to ameliorate the symptoms of an ocular disorder.

Once implanted, the drug delivery device of the invention may deliver the drug of interest over a prolonged period of time into the tissue or body fluid surrounding the device thereby imparting a localized prophylactic and/or therapeutic effect. It is contemplated that the drug delivery device may administer the drug of interest over a period of weeks (for example, 1, 2, or 3 weeks), more preferably months (for example, 1, 2, 3, 4, 5, 6, 7, 8, 9, 10, or 11 months), and most preferably years (for example, 1, 2, 3, 4, 5 years or longer).

Figure 1A:
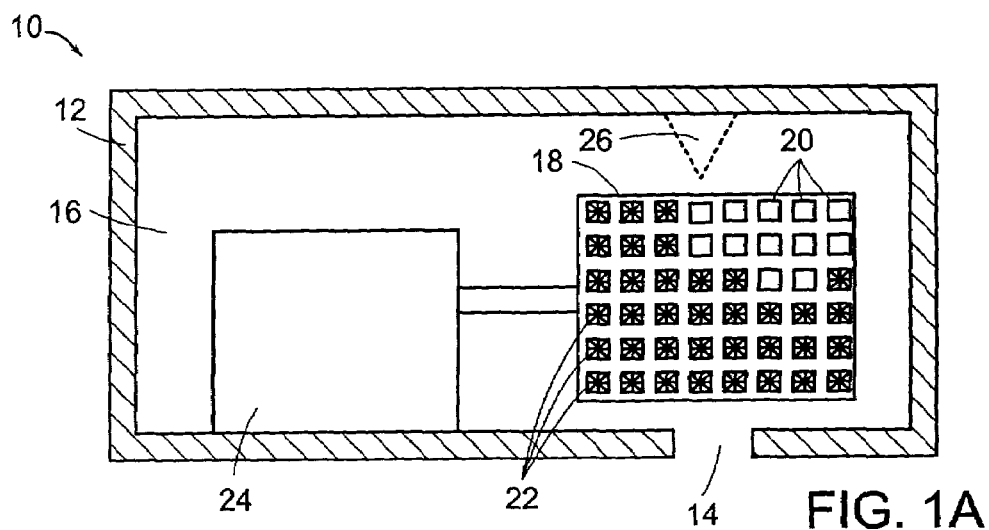
FIGS. 1A-1C are schematic illustrations of embodiments of the drug delivery device of the invention.

The miniaturized drug delivery device of the invention may be more fully understood by reference to the drawings. FIG. 1 depicts a variety of exemplary drug delivery devices of the invention. FIG. 1A depicts an implantable drug delivery device 10 having a casing 12 that defines an aperture port 14. Casing 12 further defines an inner volume 16, which optionally is in fluid flow communication with the exterior of casing 12. In such circumstances, a body fluid, for example, blood, lymph, peritoneal fluid, and uveoscleral fluid, surrounding the casing can pass into the inner volume 16 of casing 12 via aperture port 14. The device contains a reservoir member 18 that defines at least one cavity 20 for receiving the drug of interest. The drug is sealed within the cavity by seal 22. Reservoir member 18 is coupled to drive mechanism 24 for moving the reservoir member 18.

In one embodiment, drive mechanism 24 moves reservoir member, for example, via translation and/or rotation, so that an optional puncturing member 26 can contact and pierce or otherwise puncture seal 22 to release drug out of cavity 20. If body fluid is present within inner volume 16 of casing 12, then once seal 22 is punctured, cut, pierced, or otherwise broken, the drug can be dissolved by the body fluid in inner volume 16. The drug then leaves casing 12 via aperture port 14 by, for example, diffusive transport along a concentration gradient. In another embodiment, drive mechanism 24 moves reservoir member 18 so that cavity 20 containing the drug is moved adjacent to, and into alignment with and, therefore, into fluid flow communication with aperture port 14. If seal 22 is degradable, for example, fluid soluble, then once cavity 20 moves adjacent to, and into fluid flow communication with aperture port 14, body fluid present in aperture port 14 dissolves seal 22 to permit release of drug into the body fluid. Once released, the drug exits casing 12 via aperture port 14. In the latter embodiment, the other regions of the reservoir member 18 are protected from body fluid surrounding casing 12 by virtue of casing 12 being sealed and fluid impermeable.

Figure 1B:
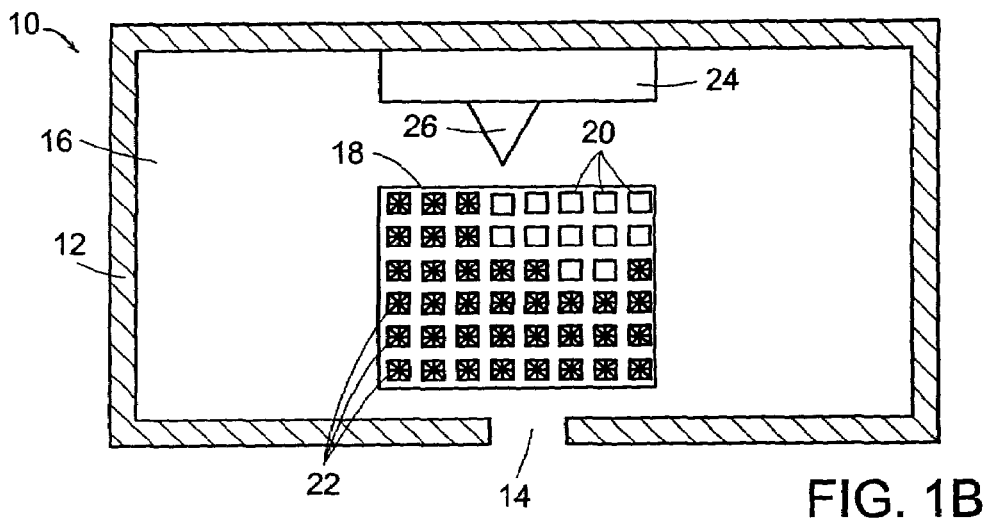

FIG. 1B depicts another implantable drug delivery device 10 having casing 12 that defines aperture port 14. Casing 12 further defines an inner volume 16, which optionally is in fluid flow communication with the exterior of casing 12. In such circumstances, a body fluid surrounding the casing can pass into and fill inner volume 16 of casing 12 via aperture port 14. The device contains reservoir member 18 that defines at least one cavity 20 for receiving the drug of interest. The drug is sealed within the cavity by a seal 22. The device also contains a puncturing member 26 coupled to a drive mechanism 24 for moving puncturing member 26, for example, via translation and/or rotation, so that puncturing member 26 can contact and pierce, cut, puncture, or otherwise degrade seal 22 to release drug out of cavity 20. If body fluid is present within inner volume 16 of casing 12, then once seal 22 is pierced, the drug can be dissolved by the body fluid in inner volume 16. Then the drug leaves casing 12 via aperture port 14 by, for example, diffusive transport along a concentration gradient.

Figure 1C:
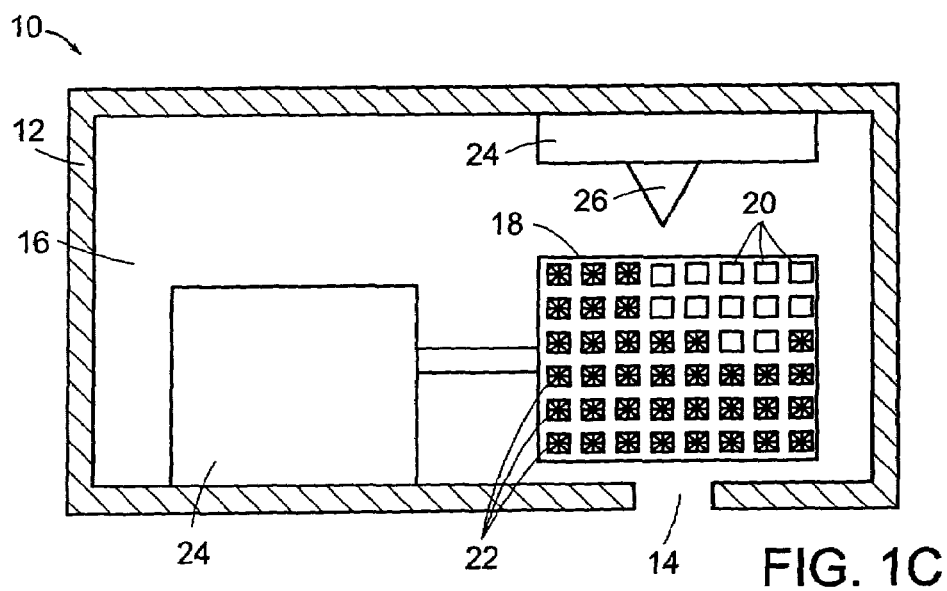

FIG. 1C depicts an implantable drug delivery device 10 having a casing 12 that defines an aperture port 14. Casing 12 further defines inner volume 16, which optionally is in fluid flow communication with the exterior of casing 12. In such circumstances, a body fluid surrounding the casing can fill inner volume 16 of casing 12 via aperture port 14. The device contains reservoir member 18 that defines at least one cavity 20 for receiving the drug of interest. Seal 22 seals the drug within the cavity. Reservoir member 18 is coupled to drive mechanism 24 for moving the reservoir member 18. Furthermore, puncturing member 26 is coupled to drive mechanism 24 for moving puncturing member 26. In one embodiment, both reservoir member 18 and puncturing member 26 are driven by the same drive mechanism. In another embodiment reservoir member 18 and puncturing member 26 are driven by separate, but preferably synchronized, drive mechanisms. Reservoir member 18 and puncturing member 26 can move, for example, rotationally and/or translationally relative to one another so that puncturing member 26 can contact and pierce, cut, puncture or otherwise degrade seal 22 to release drug out of cavity 20. If body fluid is present within inner volume 16 of casing 12, then once seal 22 is broken, the drug can be dissolved by body fluid disposed in inner volume 16. Then, the drug can leave casing 12 via aperture port 14 by, for example, diffusive transport.

The implantable drug delivery devices of the invention can be manufactured for implantation into a small cavity or space within a body. For example, the devices can be manufactured so that the device defines a total volume (i.e., via its external dimensions) of 8 cm$^3$ or less, more preferably 4 cm$^3$ or less, more preferably 1 cm$^3$ or less, more preferably 0.8 cm$^3$ or less, and most preferably 0.5 cm$^3$ or less. Such devices may be implanted into small body cavities for delivery of drug to target regions of interest. In a preferred embodiment, the drug delivery device of the invention may be adapted to deliver drug to an eyeball, wherein the device is attached to an outer surface of the eye. In such an embodiment, the device defines a total volume of preferably 0.5 cm$^3$ or less, by virtue of dimensions of, for example, approximately 1 cm (length), approximately 1 cm (width), and approximately 0.5 cm (height). As a result, the device may be attached to the outer surface of an eye. When the eye is disposed within the eye socket, the device may be accommodated at an extrascleral location posterior to the muscle insertions between the sclera and the Tenon's capsule. Furthermore, the device is designed such that when implanted, the eye is capable of relatively unrestricted movement.

Figure 2:
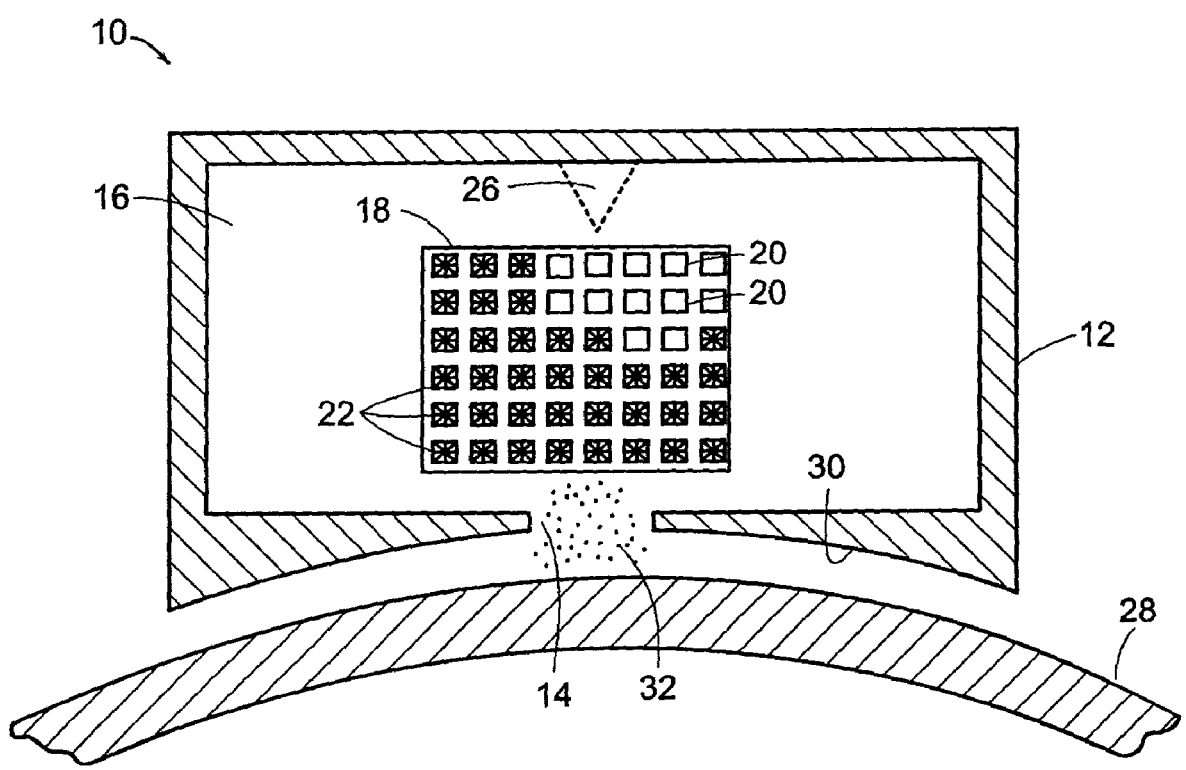
FIG. 2 is a schematic side view illustration depicting an exemplary drug delivery device of the invention attached to an outer surface of an eye.

In particular, FIG. 2 depicts a drug delivery device 10 adapted for attachment to an outer surface of eye 28 for delivering a drug into the center of the eyeball. The device can be used to treat one or more ocular diseases associated with, for example, the cornea, episclera, sclera, uvea, iris, choroid, retina, ciliary body, trabecular meshwork, and the vitreous.

The device has a casing 12 defining aperture port 14 and inner volume 16. Casing 12 also has at least one exterior surface 30 complementary in shape to the outer surface of the eye 28. The eye contacting surface of the device preferably has a concave surface having a radius of curvature complementary to the radius of curvature of the eyeball. The device contains reservoir member 18 that defines at least one cavity 20 for receiving the drug of interest. Seal 22 seals the drug of interest within the cavity. The device optionally contains a puncturing member 26 to puncture, cut, pierce otherwise degrade seal 22 to release drug 32 from the sealed cavity. If the device is configured to permit entry of body fluid into inner volume 16, then the drug can dissolve into the body fluid and then pass out of casing 12 via aperture port 14 and contact the exterior surface of the eye 28. Alternatively, when the seal is fluid degradable, reservoir member 18 moves until a sealed cavity is moved into alignment, and fluid flow communication with aperture port 14. The fluid in the aperture port then degrades or otherwise dissolves the seal to release drug 32 into the fluid disposed within aperture port 14. In either embodiment, the drug, once it contacts the exterior surface of the eye, then passes through the sclera and enters the target tissue within the eye to exert its effect.

This type of device may be useful in delivering one or more drugs of interest into an eye for ameliorating the symptoms of one or more ocular disorders including, for example, (i) ocular infections, (ii) inflammatory diseases, (iii) neoplastic diseases, and (iv) degenerative disorders. In one embodiment, the drug delivery device may be useful in the treatment of certain ocular infections, for example, infections associated with the choroid, retina and cornea. Examples include, without limitation, cytomegalovirus retinitis, tuberculous choroiditis, toxoplasma retinochoroiditis and histoplasma retinochoroiditis. In another embodiment, the drug delivery device may be useful in the treatment of inflammatory diseases, for example, inflammatory disorders associated with choroid, retina, sclera, episclera, uvea, vitreous and cornea. Examples include, without limitation, sarcoidosis, diabetic retinopathy, systemic lupus erythematosus, pars planitis, birdshot retinopathy, multifocal choroiditis and panuveitis, posterior scleritis, iritis, sympathetic ophthalmia, Harada's and Vogt-Koyanagi-Harada syndrome, subretinal fibrosis and uveitis syndrome, and white dot syndromes. In another embodiment, the drug delivery device may be useful in the treatment of neoplastic diseases, for example, neoplasia of the retina, choroid, uvea, vitreous and cornea. Examples include, without limitation, choroidal melanoma, retinoblastoma, vitreous seeding from retinoblastoma, intraocular lymphoma of the choroid, retina, or vitreous; and metastatic lesions, for example, a breast adenocarcinoma. In another embodiment, the drug delivery device may be useful in the treatment of certain degenerative disorders, for example, degenerative disorders of the retina, choroid, uvea, vitreous and cornea. Examples include, for example, macular degenerations, retinitis pigmentosa, glaucoma, and macular edema secondary to retinal vascular disorders.

In addition, the device may be used to deliver one or more drugs of interest into an eye for ameliorating the symptoms of one or more ocular disorders associated with neovascularization, including, for example, (i) ocular disorders associated with choroidal neovascularization, for example, age-related macular degeneration (more specifically, the neovascular and non-neovascular forms of age-related macular degeneration), pathologic myopia, angioid streaks, choroidal ruptures, ocular histoplasmosis syndrome, multifocal choroiditis, and idiopathic choroidal neovascularization, (ii) ocular disorders associated with corneal neovascularization, including, for example, infections, burns, certain inflammatory disorders, trauma-related disorders, and immunological disorders, (iii) ocular disorders associated with iris neovascularization, including, for example, diabetes, retinal detachment, tumors, and central retinal vein occlusion, and (iv) ocular disorders associated with retinal neovascularization including, for example, diabetic retinopathy, branch retinal vein occlusion, certain inflammatory disorders, sickle cell retinopathy, and retinopathy of prematurity.

In one embodiment, the drug delivery device comprises a rotatable reservoir member disposed within the casing. The reservoir member may be rotationally coupled, either directly or indirectly (for example, via another component, for example, a drive mechanism), to the casing. In such an embodiment, the reservoir member preferably is a rotatable drum or rotatable cylinder having one or more cavities defined by an outer surface of the drum or cylinder. FIGS. 3-5 depict such a drug delivery device.

Figure 3A:
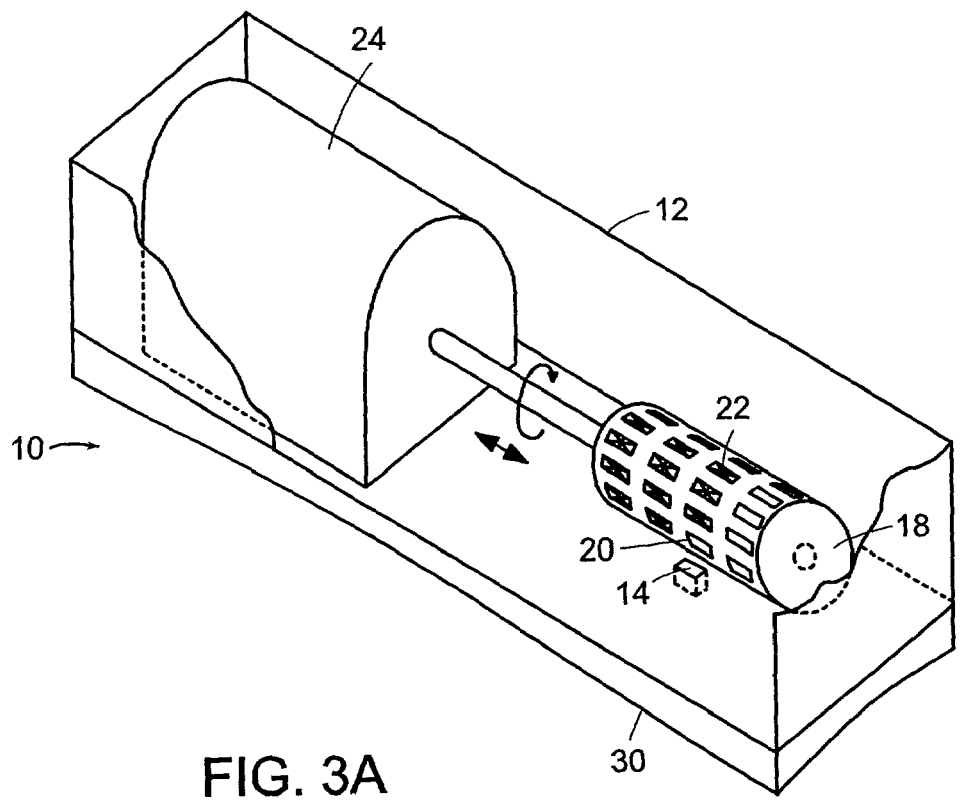
FIGS. 3A-3B are schematic illustrations of an exemplary drug delivery device of the invention employing a drum-type drug-containing reservoir member, as depicted in perspective view (FIG. 3A) and in side view (FIG. 3B).
Figure 3B:
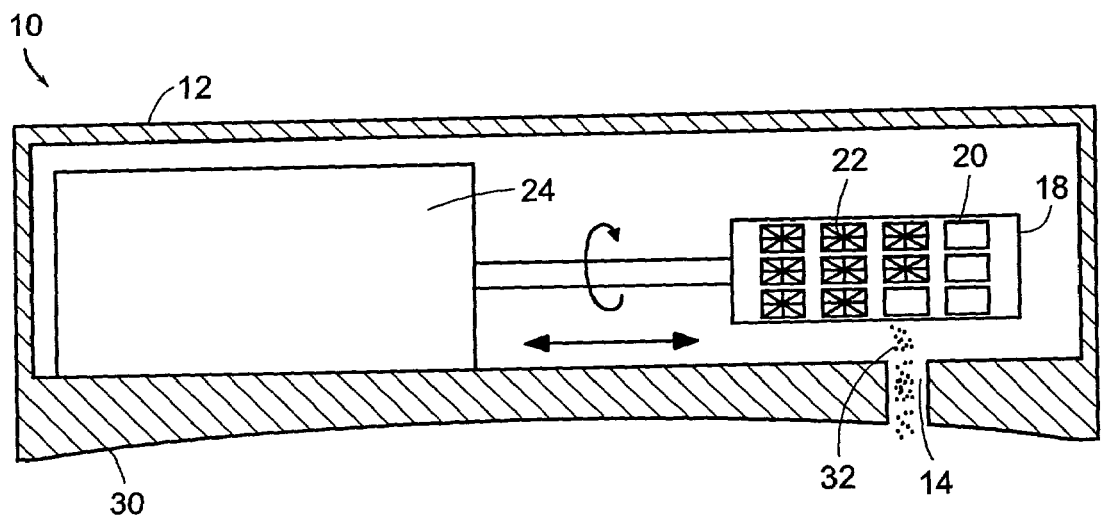

FIG. 3 shows one such embodiment of the drug delivery device 10 of the invention. In perspective view (FIG. 3A) and side view (FIG. 3B) casing 12 defines an aperture port 14 and an optional eye contacting surface 30. Reservoir member 18 in the form of a drum is rotationally and/or translationally coupled (for example, via a screw mechanism) to casing 12 via drive mechanism 24. The outer surface of the drum defines at least one cavity 20. A drug is sealed within cavity 20 by seal 22.

Depending upon the type of seal employed, the inner volume of the casing may or may not be in fluid communication with the exterior of casing. For example, where the seal is fluid degradable (for example, fluid soluble), the casing is sealed to prevent entry of fluid into the inner volume. If not, then entry of the fluid would result in simultaneous dissolution of the water soluble seals. This may be undesirable if the reservoir member contains a plurality of fluid degradable seals, all of which would start to break down at the same by virtue of simultaneous contact with the fluid. If the seal is fluid degradable, then the casing preferably is sealed and drive mechanism 24 rotates and/or translates reservoir member 18 so that cavity 20 moves from a first position spaced apart from aperture port 14 to a second position adjacent to, and in fluid communication with aperture port 14. As a result, the fluid in aperture port 14 contacts seal 22 causing it to degrade. Once degraded, the seal is broken permitting the drug to exit the cavity 20 and pass out of casing 12 via aperture port 14.

In another embodiment, seal 22 is not degraded or otherwise dissolved on contact with body fluid. As a result, body fluid enters casing 12 and, if desirable, contacts the entire outer surface of the reservoir member 18. The device preferably contains a puncturing member for puncturing or otherwise breaking the seal. Once the seal is broken, the drug can contact, and if appropriate, dissolve or solubilize in, fluid disposed with casing 12. The drug can then exit casing 12 via aperture port 14, for example, by diffusion along a concentration gradient.

Figure 4A:
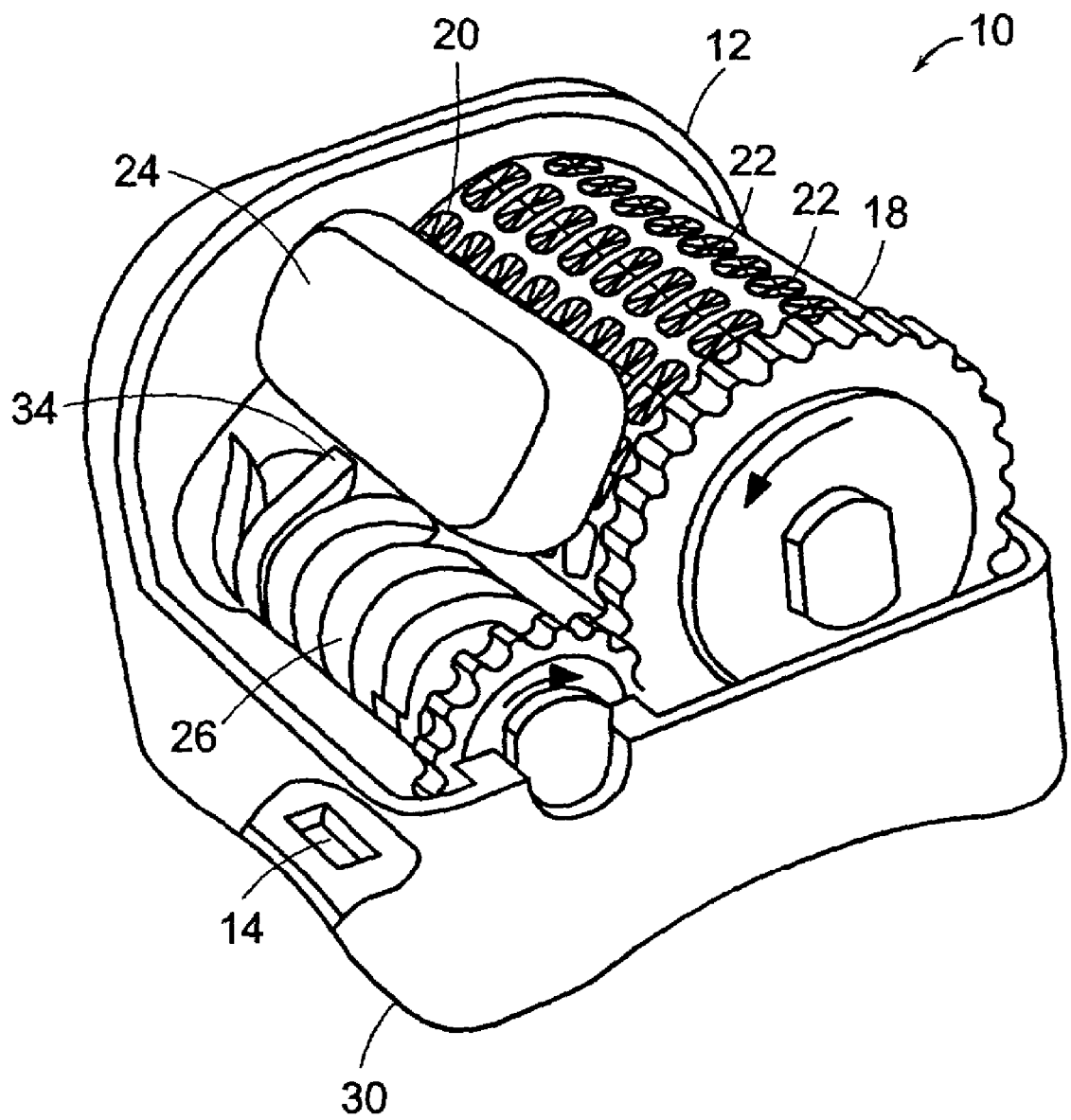
FIGS. 4A-4B are schematic illustrations of an exemplary drug delivery device of the invention employing a drum-type drug-containing reservoir member and a rotatable puncturing member.

FIG. 4 shows another embodiment of the drug delivery device 10 of the invention. In perspective view (FIG. 4A) casing 12 defines an aperture port 14 and an optional eye contacting surface 30. Reservoir member 18 in the form of a drum or cylinder can rotate relative to casing 12. Puncturing member 26 is a drum or cylinder that can rotate and/or translate relative to reservoir member 18. As shown, exemplary puncturing member 26 contains a plurality of cutting and/or piercing instruments 34 spaced apart from one another and disposed radially about an outer surface of puncturing member 26. Puncturing member 26 rotates and/or translates relative to reservoir member 18 so that sequentially one of the cutting and/or piercing instruments cuts and/or pierces a seal for a particular drug-containing cavity. Once the seal is cut and/or pierced, the drug exits the cavity and passes out of casing 12 via aperture 14. The puncturing member 26 and reservoir member 18 then rotate relative to one another so that a different cutting and/or piercing instrument is brought into contact with a different seal of a different cavity. The speed of rotation of the puncturing member 26 and reservoir member 18 relative to one another can be adjusted to cause the release of drug over a desired period of time.

Figure 4B:
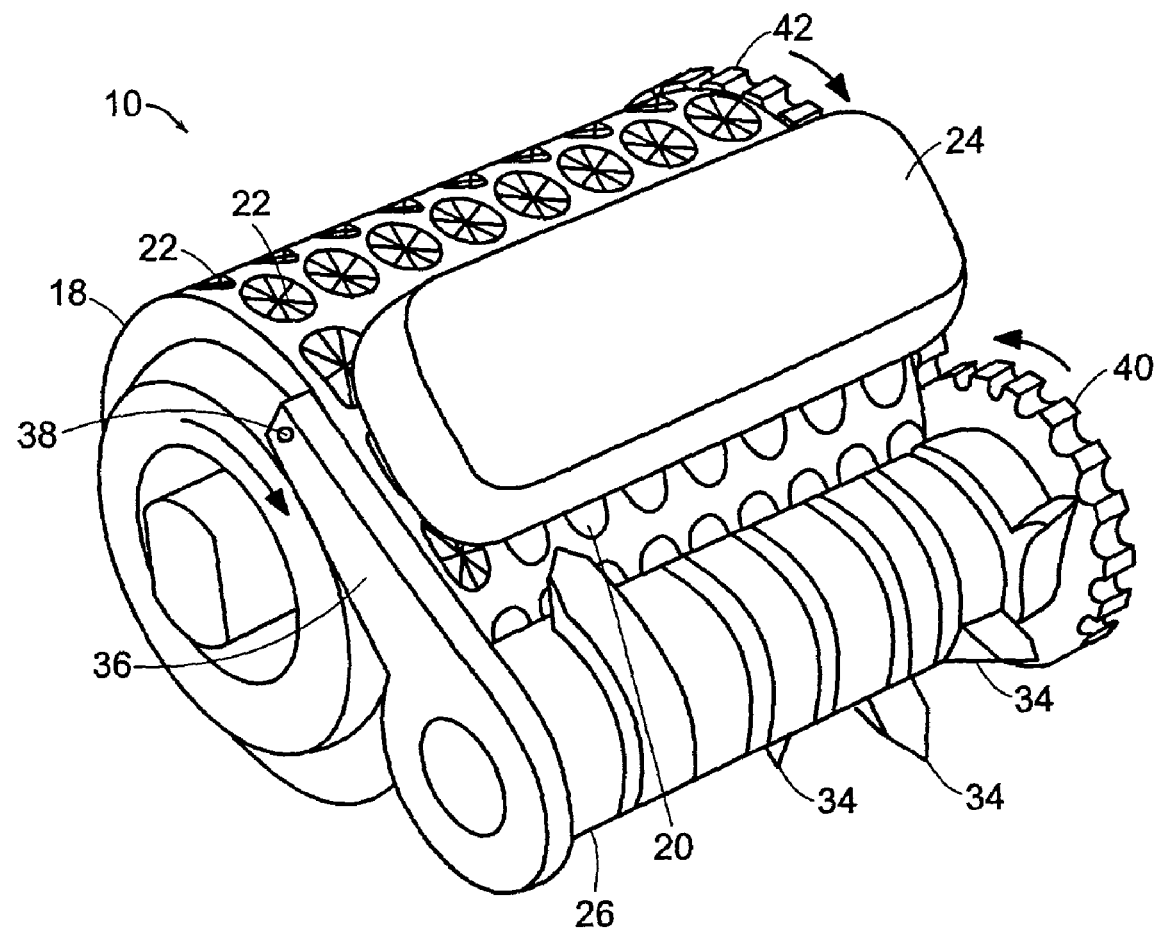
Figure 5:
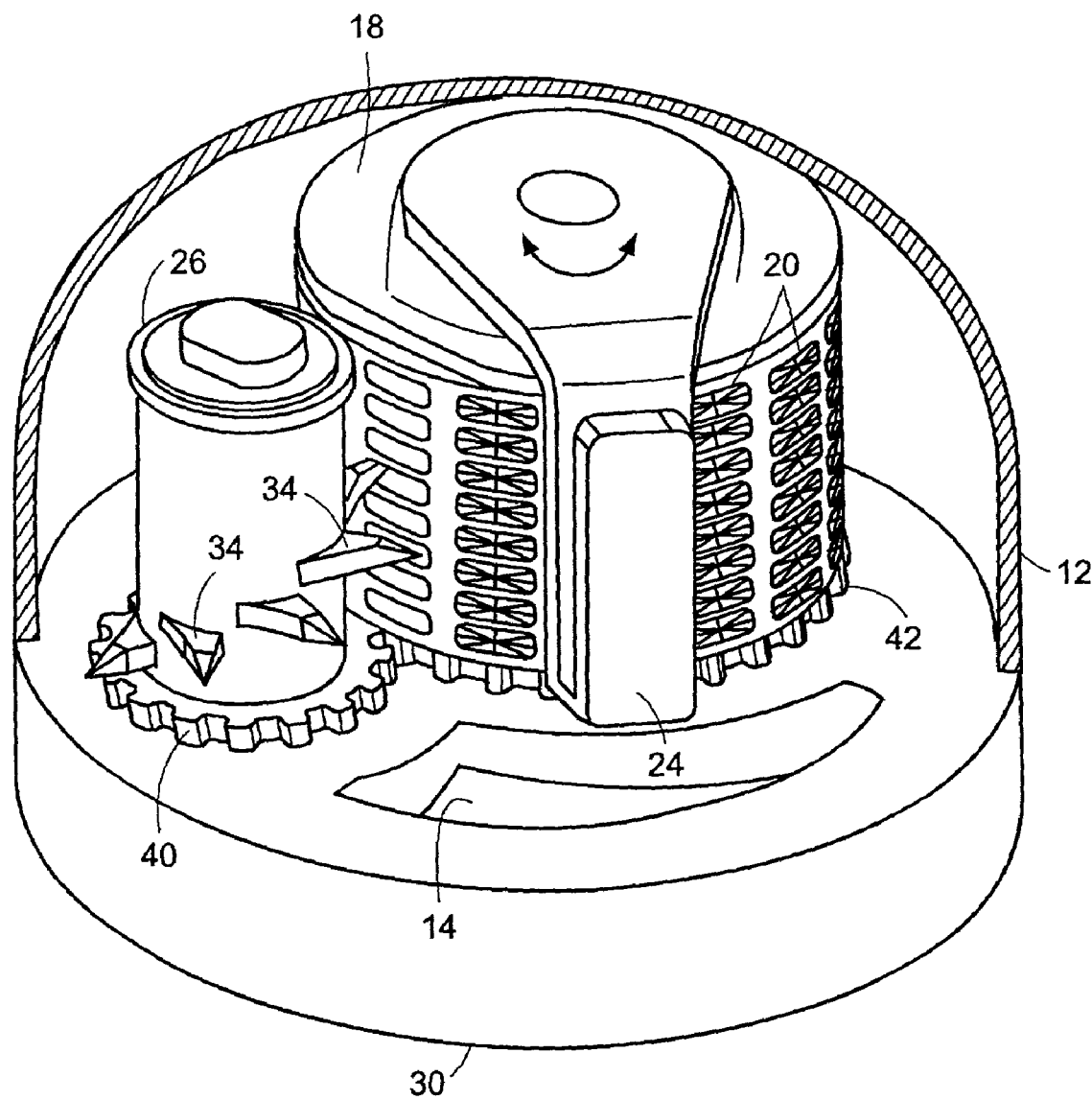
FIG. 5 is a schematic illustration in perspective view of an exemplary drug delivery device of the invention employing a drum-type drug-containing reservoir and a rotatable puncturing member.

FIG. 4A shows a single stepping mechanism (drive mechanism 24) for incrementally rotating both puncturing member 26 and reservoir member 18. FIG. 4B shows a preferred embodiment, where drive mechanism 24 comprises a power source that periodically creates a magnetic field, for example, via an immobilized coil disposed within drive mechanism 24. Coupled to puncturing member 26 is a spring biased ratchet mechanism 36 that contains a magnetic component 38 (for example, a permanent magnet). When current is applied to the coil in drive mechanism 24, it creates a magnetic field that interacts (for example, via attraction or repulsion) with the magnetic component 38 in ratchet mechanism 36 so that it moves (i) from a first position spaced apart from the coil in drive member 24 to a second position closer to the coil in drive member 24 via attraction, or (ii) from a first position in the vicinity of the coil in drive member 24 to a second position further away from the coil in drive member 24 via repulsion. Movement of ratchet mechanism 36 causes rotation of puncturing member 26. When the magnetic field is removed, ratchet mechanism 36 moves from the second position back to the first position. As this process is repeated, ratchet mechanism 36 causes incremental rotation of puncturing member 26.

As shown in FIG. 4B, the cutting and/or piercing instruments 34 rotate relative to reservoir member 18 so that a particular cutting and/or piercing instrument 34 cuts and/or pierces a seal on one of a plurality of cavities 20 disposed about the surface of reservoir member 18. Puncturing member 26 is rotationally coupled to reservoir member 18 by virtue of a gear mechanism located at one end of puncturing member 26 and at the corresponding end of reservoir member 18. Both the puncturing member 26 and the reservoir member 18 contain an intermitting, reciprocating gear mechanism 40 and 42, respectively. The gear mechanism causes puncturing member 26 and reservoir member 18 to rotate relative to one another so as to permit the cavities to be opened in a timed sequence thereby accomplishing prolonged drug delivery.

FIG. 5 shows a perspective view of another embodiment of the drug delivery device of the invention. Similar to the embodiment shown in FIG. 4, casing 12 (cut-away to reveal the inner components) defines an aperture port 14 and an optional eye contacting surface 30. In this embodiment, the rotational axes of reservoir member 18 and puncturing member 26 are disposed along a plane perpendicular to the plane defined substantially by eye contacting surface 30. Reservoir member 18, in the form of a drum cylinder, rotates relative to casing 12, and puncturing member 26. In addition, puncturing member 26, rotates incrementally relative to reservoir member 18. Puncturing member 26 contains a plurality of cutting and/or piercing instruments 34 spaced apart from one another and disposed radially about an outer surface of puncturing member 26. Rotation of puncturing member 26 relative to reservoir member 18 causes sequential cutting and/or piercing of a seal for a particular drug-containing cavity 20. A gear mechanism 40 and 42 located at one end of puncturing member 26 and at the corresponding end of reservoir member 18 causes puncturing member 26 and reservoir member 18 to rotate relative to one another so as to permit the cavities to be opened in a timed sequence. Once a seal is cut and/or pierced, the drug exits the cavity and passes out of casing 12 via aperture 14. The puncturing member 26 and reservoir member 18 then rotate relative to one another so that a different cutting and/or piercing instrument 34 is brought into contact with different seal of a different cavity 20. The speed of rotation of puncturing member 26 and reservoir member 18 relative to one another can be adjusted to cause the release of drug over a desired period of time.

In a preferred embodiment, drive mechanism 24, comprises a U-shaped pivotable member pivotably coupled to reservoir member 18. During operation, the pivotable member pivots about the drum, the motion of which is coupled, for example, via a ratchet and paul mechanism, to reservoir member 18 so as to positively drive reservoir member 18 in unilateral increments about its axis of rotation. The incremental rotation of reservoir member 18, in turn, positively drives rotation of puncturing member 26 via, for example, interfitting gear components 40 and 42.

U-shaped pivotable member preferably comprises one or more permanent magnets disposed within the U-shaped portion of the pivotable member (for example, two permanent magnets facing one another and each disposed on each side of the U-shape). Motion can be induced by induction of a magnetic field in the vicinity of the permanent magnets, thereby inducing their motion in one way or another. The magnetic field can be created by periodically passing current through an immobilized coil. For example, the immobilized coil may be attached to the interior of casing 12, and positioned so that at certain times, for example, when no magnetic field is generated by the coil, the U-shaped pivotable member can return to a position in which the coil is disposed within the central void defined by each arm of the U-shaped member.

Figure 6:
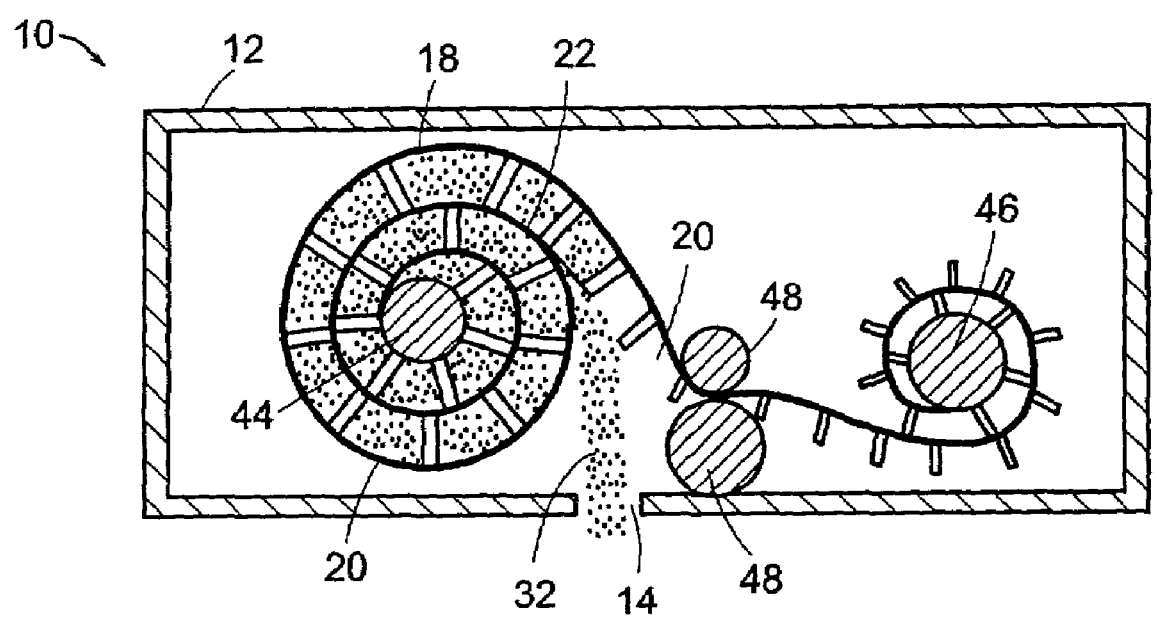
FIG. 6 is a schematic illustration depicting in side view an exemplary drug delivery device having as a drug-containing reservoir member, a flexible drug containing support member and spool assembly.

In another embodiment, the drug delivery device comprises a reservoir member that is a flexible support member (see, FIG. 6). Under certain circumstances, this configuration can permit more drug to be stored in the casing than in the rotating drum or cylinder-type embodiments. Accordingly, such a device may be able to deliver a particular drug for longer periods of time. In FIG. 6, the drug delivery device 10 comprises casing 12 defining an aperture port 14. Disposed within casing 12 is reservoir member 18 in the form of a flexible support member disposed or wrapped around a first spool 44. First spool 44 preferably is rotationally coupled (either directly or indirectly) to casing 12. The flexible support member has a surface defining a cavity 20 for receiving the drug. During operation, the flexible support member is unwound from spool 44 and cavities in the newly unwound portion of the flexible support member open to release drug 32. Once the drug has been released, the exhausted or spent portion of the flexible support member (for example, having cavities no longer containing the drug), is wrapped around a second spool 46. The device can contain a drive mechanism, for example, disposed within spool 46 to drive, for example, by pulling, the flexible support member from the first spool 44 to the second spool 46. Furthermore, the device optionally comprises one or more guide members or tensioners 48 to guide the flexible support member as it passes from first spool 44 to second spool 46.

Each of the components and methods for making and using such components are described in more detail below.

(i) Casing

Because the device of the invention is designed for implantation into a body and to the extent that the inner volume of the casing is accessible to body fluid, the choice of material for fabricating the casing and the fluid contacting surface of the inner components of the device is important. The tissue and/or body fluid contacting portions of the drug delivery device of the invention preferably are fabricated from an inert, biocompatible material. Preferred biocompatible materials include, for example, a metal, for example, gold, titanium, titanium alloy (titanium comprising 6% aluminum and 4% vanadium), nickel titanium, stainless steel, anodized aluminum, or a polymer, for example, polyethylene, polypropylene nylon, polydimethylsiloxane, polymethylmethacrylate, or polyurethane. In addition to biocompatibility, weight, strength and impermeability are all important considerations in the choice of materials. In view of the miniature nature of the drug delivery device of the invention, because of its biocompatibility, weight, fluid impermeability, and strength-to-thickness ratio, titanium is the most preferred material for the fabrication of the casing. Furthermore, to the extent that the inner volume of the casing is accessible to body fluid, the fluid contacting surfaces of the inner components, for example, the reservoir member, the power source, and drive mechanism preferably are also fabricated from titanium.

If the tissue and/or body fluid contacting portions of the device are not fabricated from biocompatible materials, then they preferably are encapsulated within a biocompatible material, such as, polyethyleneglycol, polyvinylchloride, polycarbonate, polysulfone, polytetrafluoroethylene, parylene, titanium or the like, prior to implantation.

The particular shape of the casing may be chosen depending upon the particular application. For example, the casing may have an elliptical, circular, square, or rectangular tissue contacting surface. Furthermore, when the device is adapted for attachment to the outer surface of an eye in ocular applications, the eye contacting portion of the device preferably has a shape that is complementary (i.e., a mirror image or substantially a mirror image) to the outer surface of the eye. The casing may optionally contain one or more apertures, fenestrations or eyelets to permit the device to be immobilized to the tissue of interest, for example, via sutures or the like. Furthermore, the casing may optimally comprise a rim or flange disposed about the casing as part of or adjacent to the tissue contacting surface to assist in attaching the device to the tissue of interest.

(ii) Reservoir Member and Fabrication

The reservoir member can take a variety of configurations and is adapted to receive and store the drug or drugs of interest. The reservoir member is disposed within, and preferably is operatively coupled (either directly or indirectly) to the casing. The reservoir member preferably defines a plurality of cavities, each cavity containing a dosage unit of the same drug, one of a series of different drugs, or a mixture of different drugs. In general, the materials used to fabricate or coat the reservoir member preferably are inert, biocompatible, fluid impervious, and impermeable to the drug.

Figure 7:
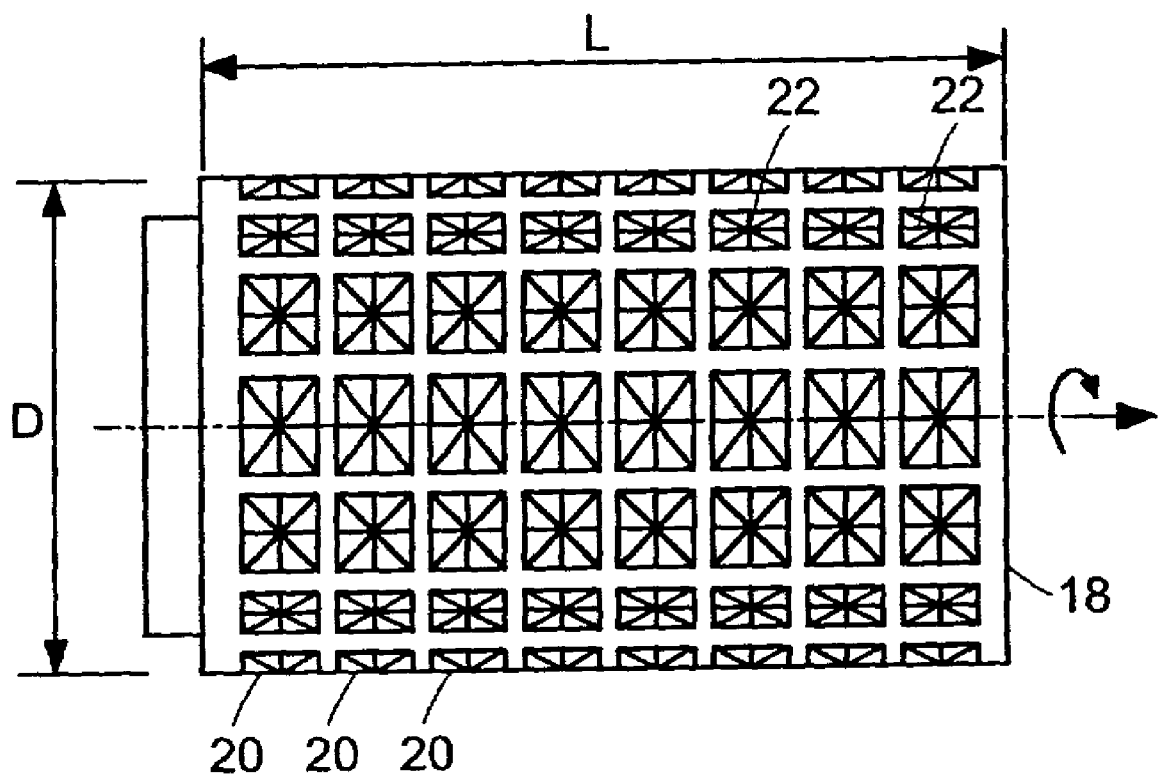
FIG. 7 depicts a schematic illustration of an exemplary drum-type reservoir member.

In a preferred embodiment, as shown schematically in FIG. 7, reservoir member 18 has a drum-like or cylindrical shape. The outer surface of the reservoir member defines a plurality of cavities 20. As shown, all of the cavities 20 are sealed with a seal 22. Reservoir member 18 has a longitudinal dimension (L) and a diametral dimension (D), and rotates about the axis, as denoted. In a preferred embodiment, drum-type reservoir member 18 has a length (L) of less than about 1.5 cm, more preferably less than about 1.0 cm, more preferably less than about 8 mm, and more preferably less than about 4 mm, and a diameter (D) of less than about 1 cm, more preferably less than about 0.8 cm, and more preferably less than about 6-7 mm. The outer surface of reservoir member 18 defines a plurality of cavities disposed around the circumference of reservoir member 18 and along the length of reservoir member 18. As a result, not all of the cavities are disposed within a single diametral plane. As used herein, the term "diametral plane" is understood to mean the plane perpendicular or substantially perpendicular to the longitudinal axis or axis of rotation of reservoir member 18. In a preferred design, each cavity has at least two non co-linear neighbors. Although the cavities shown in FIG. 7 are depicted in a substantially square array, it is contemplated that the cavities may also be disposed about the surface of the reservoir member 18 in a helical array.

Movement of such a reservoir member, if desired, may vary depending upon the particular design of the drug delivery device of the invention. For example, the reservoir member may rotate and/or translate relative to the device casing and/or the puncturing member. In one embodiment, the reservoir member both rotates and translates relative to the casing. See, for example, FIG. 3B, where reservoir member 18 is coupled to drive mechanism 24 via a screw mechanism. Depending upon the direction of rotation, as reservoir member 18 rotates it moves either away from or closer to drive mechanism 24. In another embodiment, as shown in FIGS. 4A and 5, the reservoir simply rotates relative to casing 12 and puncturing member 26.

It is contemplated that materials useful in the fabrication of reservoir member 18 may be the same as those useful in the fabrication of the casing, as previously discussed. In a preferred embodiment, however, the reservoir member is fabricated from titanium. Furthermore, it is contemplated that the drum or cylindrical-type of reservoir member can take a variety of different forms. For example, reservoir member 18 may be solid or hollow. Hollow members are preferred when weight is a significant concern or a where a puncturing member acts on a base of the cavity to break the seal (see, for example, FIG. 9B).

The cavities may be fabricated using a variety of different techniques, the choice of which may depend, for example, upon the size of the cavity, the location and spatial relationships of the different cavities, and the mechanism used to fill each cavity with drug. For example, the cavities may be drilled or milled into the surface of the drum-type reservoir member 18. Alternatively, the cavities may be formed in a planar, compliant material, which after fabrication (and optionally after each cavity has been filled with drug and sealed) is wrapped around the surface of the drum-type reservoir member.

Figure 8A:
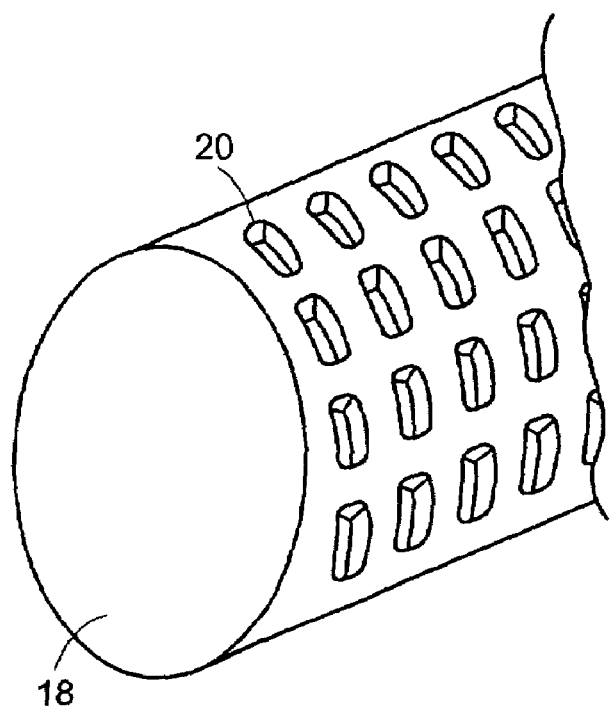
FIGS. 8A-8B are schematic illustrations of cavities that can be employed in conjunction with a drug-containing reservoir member.
Figure 8B:
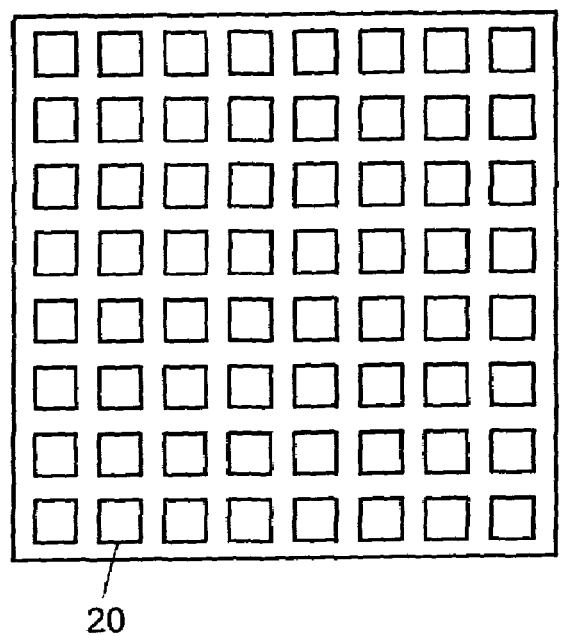

FIGS. 8A and 8B are schematic illustrations depicting different ways for fabricating cavities within the outer surface of the reservoir member. FIG. 8A depicts a drum-type reservoir member 18 in which cavities 20 have been drilled into the surface of a drum. It is contemplated that in addition to drilling, such cavities may be formed by dry milling, hot embossing, solid free-form fabrication, laser machining and other techniques known in the art. In a preferred embodiment, the cavities are micro-machined into titanium. Furthermore, in a preferred embodiment, each cavity is machined to define an internal volume of from about 0.1 µL to about 1.5 µL, preferably from about 0.2 µL to about 1.0 µL, and more preferably from about 0.3 µL to about 0.7 µL. In a preferred embodiment, the drum has, for example, 120 cavities disposed about the outer surface thereof in an array in which 8 rows of cavities are disposed along the length of the drum and 15 rows of cavities are disposed about the circumference of the drum. However, the size, capacity, and number of cavities disposed about a reservoir member will depend upon the drug regime to be administered. Upon fabrication, the cavities defined by the reservoir member are filled with the drug or drugs of interest and sealed prior to use.

In another approach, the cavities may be defined by a compliant matter, which after fabrication can be wrapped around and attached to the outer surface of the drum-type reservoir member. For example, FIG. 8B depicts a planar sheet of pliable, compliant material defining cavities 20 that can be wrapped around a drum-type reservoir member. The planar sheet can be formed by a variety of techniques known in the art, including, for example, contact replica molding, micro-printing, injection molding, or the like. For example, during a molding procedure a mold having the appropriate dimensions is created, for example, in a metal, silicon or glass substrate using, for example, standard machining, standard lithography and/or anisotropic silicon etching techniques. Once the mold has been created, a material suitable for forming the planar material, for example, a polymer such as polydimethylsiloxane (PDMS) elastomer, or silicone then is poured into the mold. After curing, the planar sheet is removed from the mold.

Upon fabrication, the cavities defined by the reservoir member are filled with the drug or drugs of interest and sealed prior to use. It is contemplated that the cavities can be filled with drug and then sealed while in planar form. Alternatively, the planar sheet can be wrapped around the reservoir member, after which the cavities can be filled with drug and then sealed. Irrespective of the timing of filling and sealing of the cavities, the compliant sheet is wrapped or rolled around the surface of the reservoir member. The sheet can be attached or bonded to the reservoir member by activating the surface using, for example, an oxygen plasma for the compliant polymer sheet, or by using a glue or adhesive, such as, cyanoacrylate.

The cavities can be disposed within the planar sheet, so that when the sheet is wrapped around a cylindrical reservoir member, the cavities are disposed within a square array. Alternatively, the cavities can be disposed within the planar array slightly offset with respect to one another, so that when the sheet is wrapped around a cylindrical reservoir member, the cavities are helically disposed about the surface of the reservoir member.

In one embodiment, the reservoir member is a drum and the cavity seal is fluid degradable (see, FIG. 9A), for example, the seal dissolves or breaks down when in contact with fluid. In such a case, the planar sheet may be fabricated as above. A hydrophobic layer then is deposited, patterned and etched so that the cavities remain unsealed. After each cavity is filled with drug, a hydrophilic layer then is patterned and etched to provide a hydrophilic, degradable seal over the cavity. The resulting flexible polymer sheet then is wrapped or rolled around the outer surface of the cylindrical drum and attached using a suitable bonding mechanism or adhesive material.

Figure 9A:
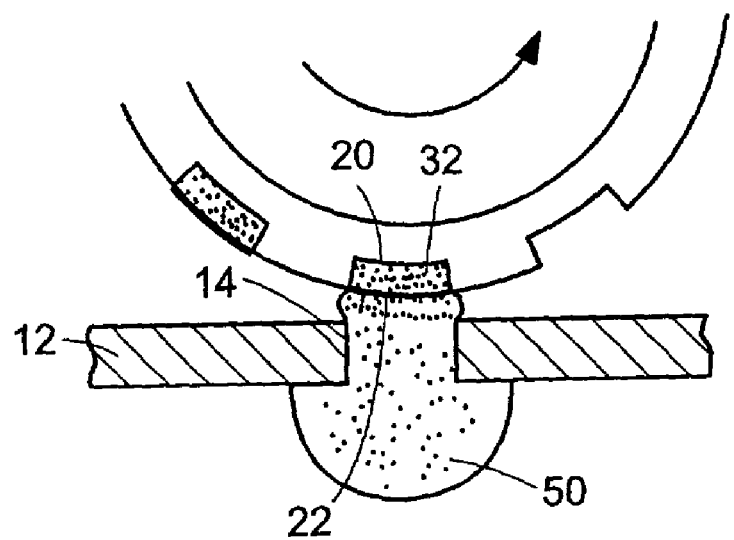
FIGS. 9A-9D are schematic illustrations that depict various exemplary mechanisms for breaking cavity seals, including a side view of a degradable seal (FIG. 9A), a side view of a spring loaded cantilever (FIG. 9B), a side view of a fixed or translating puncturing member (FIG. 9C), and a front view of a rotating puncturing member (FIG. 9D).
Figure 9B:
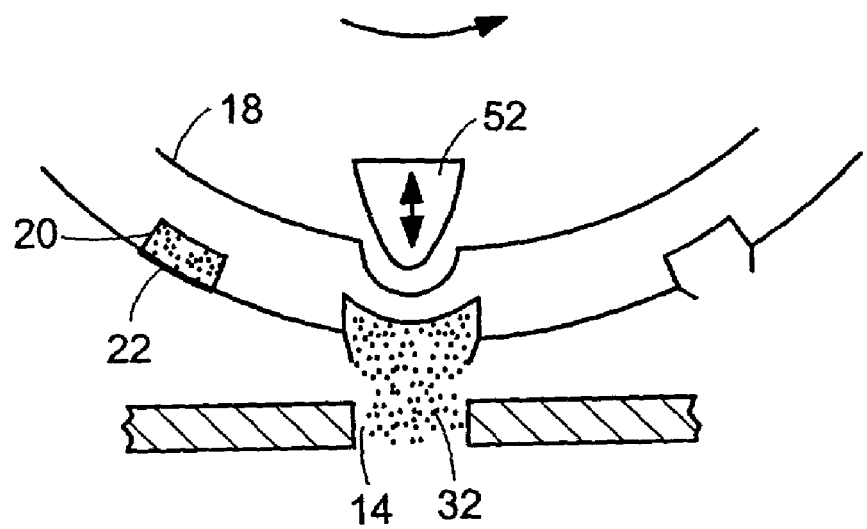

In another embodiment, the reservoir member is a hollow drum and the cavity seal is broken by application of pressure to the base of the cavity via a cantilever-type puncturing member (see, FIG. 9B). In this embodiment, the cantilever-type puncturing member moves in a plane perpendicular to the plane defined substantially by base of the cavity. When the puncturing member is in contact with the base, an increase in internal pressure within the cavity causes the seal to break releasing drug out of the cavity. The planar sheet can be fabricated to provide a hollow cylinder with the cavity seals disposed on the outer circumference of the cylinder. A variety of approaches can be used to ensure that the planar sheet forms a cylinder. For example, the planar sheet can be rolled around a cylindrical support with holes aligned relative to cavities defined by the planar sheet. The cylindrical support then remains and defines part of the cylindrical reservoir member. In another approach, the planar sheet is wrapped around an erodable rigid cylinder. The cylinder then is encased within a wire mesh frame that maintains the shape of the cylinder and then the erodable rigid cylinder is removed. As an alternative approach, a cylinder having the requisite diameter is dipped into a moldable polymer, such as, PDMS. After curing, cavities are etched into the polymer coating using, for example, three-dimensional lithography and/or laser drilling.

In another embodiment, the reservoir member is a flexible support member that is wrapped around a spool or spindle assembly (see, FIG. 6). The flexible support member is a tape-like strip, one surface of that defines a plurality of cavities sequentially spaced apart from one another. In one embodiment, the flexible support member is formed via molding, using a moldable polymer, such as PDMS, as a substrate. The techniques described above for the PDMS drum are applicable here. Once formed, the cavities of the flexible support member are filled with drug. Once fabricated, flexible support member then is wound around the spool or spindle for use. The winding process can generate a seal by virtue of closing a cavity with an adjacent layer of the flexible support member.

(iii) Drug and Drug Formulation

It is understood that the drug delivery device of the invention can be used to deliver one or more drugs to a particular target site. The drug can be disposed within the cavity in solid, liquid or gel form. As used herein, the term "drug" is understood to mean any natural or synthetic, organic or inorganic, physiologically or pharmacologically active substance capable of producing a localized or systemic prophylactic and/or therapeutic effect when administered to an animal. A drug includes (i) any active drug, (ii) any drug precursor or pro-drug that may be metabolized within the animal to produce an active drug, (iii) combinations of drugs, (iv) combinations of drug precursors, (v) combinations of a drug with a drug precursor, and (vi) any of the foregoing in combination with a pharmaceutically acceptable carrier, excipient or formulating agent.

The drug may include, for example, a protein (for example, an antibody or an antigen binding portion thereof), a polypeptide, a nucleic acid (for example, deoxyribonucleic acid and/or ribonucleic acid), a peptidyl nucleic acid, a polysaccharide, a fatty acid (for example, prostaglandin), an organic molecule and an inorganic molecule, that has prophylactic and/or therapeutic value, i.e., elicits a desired effect, when administered to an animal. The drug can include, for example, a hormone or synthetic hormone, an anti-infective agent (for example, an antibiotic, an anti-viral agent, and an anti-fungal agent), a chemotherapeutic agent (for example, methotrexate, chlorambucil, cyclosporine, and interferon), an autonomic drug (for example, an anticholinergic agent, adrenergic agent, adrenergic blocking agent, and a skeletal muscle relaxant), a blood formation or blood coagulation modulating agent (for example, an anti-anemia drug, coagulant and an anti-coagulant, hemorrhagic agent, and a thrombolytic agent), a cardiovascular drug (for example, a hypotensive agent, vasodilating agent, inotropic agent, β-blocker, and a sclerosing agent), a central nervous system agent (for example, an analgesic, an antipyretic, and an anti-convulsant), an immunomodulating agent (for example, etanercept, or an immunosuppresant), an anti-inflammatory agent (for example, a steroid, and interferon α), an anti-obesity agent (for example, leptin), an anti-lipemic agent (for example, an inhibitor of hydroxymethyl-glutaryl co-enzyme A reductase), an anti-emetic agent (for example, cisapride and metoclopramide), an anti-migraine medication (for example, imitrex), a chelating agent (for example, the iron chelator desferoxamine), and a contraceptive or fertility agent.

The drug also embraces an angiogenesis inhibitor, i.e., a compound that reduces or inhibits the formation of new blood vessels in a mammal. Angiogenesis inhibitors may be useful in the treatment of various disorders associated with neovascularization, for example, certain ocular disorders associated with neovascularization. Examples of useful angiogenesis inhibitors, include, for example, protein/peptide inhibitors of angiogenesis such as: angiostatin, a proteolytic fragment of plasminogen (O'Reilly et al. (1994) CELL 79: 315-328, and U.S. Pat. Nos. 5,733,876; 5,837,682; and 5,885,795) including full length amino acid sequences of angiostatin, bioactive fragments thereof, and analogs thereof; endostatin, a proteolytic fragment of collagen XVIII (O'Reilly et al. (1997) CELL 88: 277-285, Cirri et al. (1999) INT. BIOL. MARKER 14: 263-267, and U.S. Pat. No. 5,854,205) including full length amino acid sequences of endostatin, bioactive fragments thereof, and analogs thereof; peptides containing the RGD tripeptide sequence and capable of binding the α-,β$_3$ integrin (Brooks et al. (1994) CELL 79: 1157-1164, Brooks et al. (1994) SCIENCE 264: 569-571); certain antibodies and antigen binding fragments thereof and peptides that bind preferentially to the α-,β$_3$ integrin found on tumor vascular epithelial cells (Brooks et al., supra, Friedlander et al. (1996) PROC. NATL. ACAD. SCI. USA 93: 9764-9769); certain antibodies and antigen binding fragments thereof and peptides that bind preferentially to and block or reduce the binding activity of the Epidermal Growth Factor receptor (Ciardiello et al. (1996) J. NATL. CANCER INST. 88: 1770-1776, Ciardiello et al. (2000) CLIN. CANCER RES. 6:3739-3747); antibodies, proteins, peptides and/or nucleic acids that preferentially bind to and inhibit or reduce the activity of Vascular Endothelial Growth Factor (VEGF) (Adamis et al. (1996) ARCH OPTHALMOL 114: 66-71), antibodies, proteins, and/or peptides that preferentially to and block or reduce the binding activity of Vascular Endothelial Growth Factor receptor; anti-Fibroblast Growth Factor, anti-Epidermal Growth Factor (Ciardiello et al. (2000) CLIN. CANCER RES. 6: 3739-3747) including full length amino acid sequences, bioactive fragments and analogs thereof, and Pigment Epithelium-derived Growth Factor (Dawson (1999) SCIENCE 2035: 245-248) including full length amino acid sequences, bioactive fragments and analogs thereof. Bioactive fragments refer to portions of the intact protein that have at least 30%, more preferably at least 70%, and most preferably at least 90% of the biological activity of the intact proteins. Analogs refer to species and allelic variants of the intact protein, or amino acid replacements, insertions or deletions thereof that have at least 30%, more preferably at least 70%, and most preferably 90% of the biological activity of the intact protein.

Other angiogenesis inhibitors include, for example, COX-2 selective inhibitors (Masferrer et al. (1998) PROC. AMER. ASSOC. CANCER RES. 39: 271; Ershov et al. (1999) J. NEUROSCI. RES. 15: 254-261; Masferrer et al. (2000) CURR. MED. CHEM. 7: 1163-1170); tyrosine kinase inhibitors, for example, PD 173074 (Dimitroff et al. (1999) INVEST. NEW DRUGS 17: 121-135), halofuginone (Abramovitch et al. (1999) NEOPLASIA 1: 321-329; Elkin et al. (1999) CANCER RES. 5: 1982-1988), AGM-1470 (Brem et al. (1993) J. PED. SURGERY 28: 1253-1257), angiogenic steroids, for example, hydrocortisone and anecortave acetate (Penn et al. (2000) INVEST. OPHTHALMOL. VIS. SCI. 42: 283-290), thrombospondin-1 (Shafiee et al. (2000) INVEST. OPHTHALMOL. VIS. SCI. 8: 2378-2388; Nor et al. (2000) J. VASC. RES. 37: 09-218), UCN-01 (Kruger et al. (1998-1999) INVASION METASTASIS 18: 209-218), CM101 (Sundell et al. (1997) CLIN. CANCER RES. 3: 365-372); fumagillin and analogues such as AGM-1470 (Ingber et al. (1990) NATURE 348: 555-557), and other small molecules such as thalidomide (D'Amato et al. (1994) PROC. NATL. ACAD. SCI. USA 91: 4082-4085).

Several cytokines including bioactive fragments thereof and analogs thereof have also been reported to have anti-angiogenic activity and thus may be delivered using the device of the invention. Examples include, for example, IL-12, which reportedly works through an IFN-γ-dependent mechanism (Voest et al. (1995) J. NATL. CANC. INST. 87: 581-586); IFN-α, which has been shown to be anti-angiogenic alone or in combination with other inhibitors (Brem et al. (1993) J. PEDIATR. SURG. 28: 1253-1257). Furthermore, the interferons IFN-α, IFN-β and IFN-γ reportedly have immunological effects, as well as anti-angiogenic properties, that are independent of their anti-viral activities.

It is contemplated that useful angiogenesis inhibitors, if not already known, may be identified using a variety of assays well known and used in the art. Such assays include, for example, the bovine capillary endothelial cell proliferation assay, the chick chorioallantoic membrane (CAM) assay or the mouse corneal assay. However, the CAM assay is preferred (see, for example, O'Reilly et al. (1994) CELL 79: 315-328 and O'Reilly et al. (1997) CELL 88: 277-285). Briefly, embryos with intact yolks are removed from fertilized three day old white eggs and placed in a petri dish. After incubation at 37° C., 3% $CO_2$ for three days, a methylcellulose disk containing the putative angiogenesis inhibitor is applied to the chorioallantoic membrane of an individual embryo. After incubation for about 48 hours, the chorioallantoic membranes are observed under a microscope for evidence of zones of inhibition.

The drug also embraces a neuroprotective agent, i.e., an agent capable of retarding, reducing or minimizing the death of neuronal cells. Neuroprotective agents may be useful in the treatment of various disorders associated with neuronal cell death, for example, certain ocular disorders including, for example, macular degeneration, retinitis pigmentosa, glaucoma and diabetic retinopathy. Examples of neuroprotective agents include, for example, apoptosis inhibitors, for example, neurotrophic factors, cAMP elevating agents, and caspase inhibitors.

Exemplary neurotrophic factors include, for example, Brain Derived Growth Factor and bioactive fragments and analogs thereof (Caffe et al. (2001) INVEST OPHTHALMOL VIS SCI. 42: 275-82); Fibroblast Growth Factor and bioactive fragments and analogs thereof (Bryckaert et al. (1999) ONCOGENE 18: 7584-7593); Pigment Epithelium Derived Growth Factor and bioactive fragments and analogs thereof; and Insulin-like Growth Factors (IGF) and bioactive fragments and analogs thereof, for example, IGF-I and IGF-II (Rukenstein et al. (1991) J. NEUROSCI. 11: 552-2563) and cytokine-associated neurotrophic factors. Exemplary cAMP elevating agents include, for example, 8-(4-chlorophenylthio)-adenosine-3': 5'-cyclic-monophosphate (CPT-cAMP) (Koike (1992) PROG. NEURO-PSYCHOPHARMACOL AND BIOL. PSYCHIAT. 16: 95-106), forskolin, isobutyl methylxanthine, cholera toxin (Martin et al. (1992) J. NEUROBIOL 23: 1205-1220), 8-bromo-cAMP, $N^6$, $O^{2'}$-dibutyryl-cAMP and $N^6,O^{2'}$ dioctanoyl-cAMP (Rydel and Greene (1988) PROC. NAT'L. ACAD. SCI. USA 85: 1257-1261). Exemplary caspase inhibitors include, for example, caspase-1 inhibitors, for example, Ac—N-Me-Tyr-Val-Ala-Asp-aldehyde, caspase-2 inhibitors, for example, Ac-Val-Asp-Val-Ala-Asp-aldehyde, caspase-3 inhibitors, for example, Ac-Asp-Glu-Val-Asp-aldehyde, caspase-4 inhibitors, for example, Ac-Leu-Glu-Val-Asp-aldehyde, caspase-6 inhibitors, for example, Ac-Val-Glu-Ile-Asp-aldehyde, caspase-8 inhibitors, for example, Ac-Asp-Glu-Val-Asp-aldehyde, and caspase-9 inhibitors, for example, Ac-Asp-Glu-Val-Asp-aldehyde, each of which can be obtained from Bachem Bioscience Inc., PA.

As discussed, the device of the invention is useful in the treatment of a variety of ocular disorders. For example, the drug delivery device may deliver an anti-infective agent, such as, an antibiotic, anti-viral agent or anti-fungal agent, for the treatment of an ocular infection. Similarly, the device may deliver a steroid, for example, hydrocortisone, dexamethasone sodium phosphate or methylprednisolone acetate, for the treatment of an inflammatory disease of the eye. The device may be used to deliver a chemotherapeutic or cytotoxic agent, for example, methotrexate, chlorambucil, cyclosporine, or interferon, for the treatment of an ocular neoplasm. Furthermore, the device may be useful in delivering one or more drugs for the treatment of certain degenerative ocular disorders, for example, (i) an adrenergic agonist, such as, epinephrine (Epifrin), dipivefrin (Propine), apraclonidine (Iopidine), or brimonidine (Alphgan); a β-blocker, such as, betaxolol (Betoptic) or timolol (Timoptic); a carbonic anhydrase inhibitor, such as, acetazolamide (Diamox), methazolamide (Neptazane), dorzolamide (Trusopt), or brinzolamide (Azopt); prostglandin analogues, such as, latanoprost (Xalatan), for the treatment of glaucoma, (ii) an integrin (such as, a lymphocyte function associated molecule (LFA-1), Mac-1 or p150,95) antagonist; a selectin (such as, E-selectin, P-selectin and L-selectin) antagonist; an adhesion molecule (such as, an intercellular Adhesion molecule (ICAM)-1, ICAM-2, ICAM-3) antagonist; a Platelet Endothelial Adhesion Molecule antagonist; a Vascular Cell Adhesion Molecule antagonist; a leukocyte adhesion inducing cytokine or growth factor (such as, Tumor Necrosis Factor-α, or Interleukin-1β) antagonist; a Monocyte Chemotactic Protein-1 antagonist; a VEGF antagonist, and other molecules described in PCT/US99/31215 for the treatment of diabetic retinopathy, (iii) an anti-inflammatory drug, such as, a steroid (for example, hydrocortisone, dexamethasone sodium phosphate or methylprednisolone acetate), indomethacin, naprosyn, or a VEGF antagonist for the treatment of macular edema secondary to certain retinal vascular disorders. As used herein, the antagonist may comprise, without limitation, an antibody, an antigen binding portion thereof or a biosynthetic antibody binding site that binds a particular target protein, for example, ICAM-1; an antisense molecule that hybridizes in vivo to a nucleic acid encoding a target protein or a regulatory element associated therewith, or a ribozyme, aptamer, or small molecule that binds to and/or inhibits a target protein, for example, ICAM-1, or that binds to and/or inhibits, reduces or otherwise modulates expression of nucleic acid encoding a target protein, for example, ICAM-1.

The drug or drugs of interest may be introduced into a cavity either in pure form or as a formulation, for example, in combination with a pharmaceutically acceptable carrier or encapsulated within a release system. A release system can include a matrix of a biodegradable material or a material which releases incorporated drug by diffusion. The drugs can be homogeneously or heterogeneously distributed within the release system. A variety of release systems may be useful in the practice of the invention, however, the choice of the appropriate system will depend upon rate of drug release required by a particular drug regime. Both non-degradable and degradable release systems can be used. Suitable release systems include polymers and polymeric matrices, non-polymeric matrices, or inorganic and organic excipients and diluents such as, but not limited to, calcium carbonate and sugar. Release systems may be natural or synthetic. However, synthetic release systems are preferred because generally they are more reliable, more reproducible and produce more defined release profiles. The release system material can be selected so that drugs having different molecular weights are released from a particular cavity by diffusion through or degradation of the material. Biodegradable polymers, bioerodible hydrogels, and protein delivery systems currently are preferred for drug release via diffusion or degradation.

Representative synthetic, biodegradable polymers include, for example: polyamides such as poly(amino acids) and poly(peptides); polyesters such as poly(lactic acid), poly(glycolic acid), poly(lactic-co-glycolic acid), and poly(caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly(ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

(iv) Cavity Filling

The drug delivery device of the invention may be used to deliver one or more drugs to a target tissue over a prolonged period of time. It is contemplated that one type of drug can be sealed within a particular cavity of the reservoir member. However, it is contemplated that a plurality of drugs may be sealed within a single cavity so that they are all released from the reservoir member at the same time. Alternatively, a first drug may be sealed within one cavity and a second, different drug may be sealed within a second, different cavity. The last approach permits two drugs to be delivered to the target site at different times.

The drug may be loaded into the cavities using conventional procedures known in the art. When the drug is in a liquid form, the cavity may be filled, for example, by a conventional micropipette system, for example, the syringe-pumped Biojet dispenser (BioDot, Inc., Irvine, Calif.). The drug may then be dried in the cavity, for example, by freeze-drying or evaporative drying. When the drug is in dry form, the cavity may be filled by, for example, dry packing.

It is understood, however, that the choice of a drug, its formulation, and loading into the different cavities of the reservoir will depend upon the particular prophylactic or therapeutic regime to be achieved.

(v) Cavity Sealing and Seal Breakage Mechanisms

After each cavity has been filled with the drug of interest, the drug then is sealed within the cavity with a seal. It is understood that the choice of seal and seal breakage mechanism are interrelated.

The seal may be integral with the reservoir member, may be a coating applied uniformly about the surface of the reservoir member, or may be formed separately from the reservoir member and then attached to the reservoir member to seal the drug within the cavity. In general, it is contemplated that two types of seals are useful in the practice of the invention. One type of seal dissolves or breaks down upon contact to a fluid. When exposed to fluid, such a seal dissolves or breaks down to permit drug disposed within the cavity to come into contact with body fluid, for example, body fluid disposed within the aperture port of the casing. The other type of seal does not dissolve or break down upon contact to a fluid. This type of seal, therefore, requires, for example, a mechanical or electrochemical procedure to break the seal and release the drug within the cavity.

When the seals are designed for dissolution or breakage upon exposure to a degrading medium, such as a body fluid, the seal preferably is fabricated from a polymeric material or a combination of polymeric materials selected to achieve a degradation rate of interest. It is possible to fabricate different seals so that they break down and release drug over different time frames. Differential drug release can be achieved using a variety of different approaches. In one approach, the seal for one cavity is fabricated from a first material and a seal for a different cavity is fabricated from a second, different material. Alternatively, the seals may be fabricated from the same material or set of materials but with modification to modulate to the rate of dissolution of one type of seal relative to another type of seal. For example, when the seal is a polymer, one approach is to adjust the level of cross-linking in, and/or thickness of one seal relative to another seal. Any combination of polymer, degree of crosslinking, or polymer thickness can be modified to obtain a specific release time of interest.

FIG. 9A depicts such a mechanism of seal breakage. Cavity seal 22 is fabricated from a fluid degradable, for example, fluid soluble, material. In this approach, the seal is fabricated from and/or coated with a hydrophilic material, for example, polyethylene glycol. In contrast, the other portions of the reservoir member are fabricated from, or coated with a hydrophobic material, for example, a saturated hydrocarbon. In this approach, body fluid 50 enters aperture port 14 and can then contact seal 22 as cavity 20 moves into fluid flow communication with aperture port 14. When wetted, seal 22 begins to degrade. When degraded sufficiently, drug 32 exits cavity 20, and then casing 12 via aperture port 14. Incremental rotation of reservoir member 18 causes a hydrophobic surface (for example, a portion of the surface of the drum interposed between the cavities) to be positioned adjacent aperture port 14. As a result, fluid 50 is sheared from the previous cavity 20 and re-beads. Further rotation brings the next cavity 20 into alignment and fluid flow communication with aperture port 14, and the process is repeated. In a preferred embodiment, the outer surface of the casing, the walls of the aperture port and the seal are all fabricated from or coated with a hydrophilic material, whereas the inner surface of the casing and the outer surfaces of all of the other inner components of the device (other than the seal) are fabricated from or coated with a hydrophobic material.

In another approach, the seal is broken down via an electrochemical process, for example, by applying an electrical potential across the seal. In this embodiment, the cavity seal comprises a thin film of conductive material patterned, for example, as an anode surrounded by cathodes in the portions of the drug reservoir surrounding the cavity. For this approach, preferred seals are fabricated from metallic materials, such as copper, gold, silver and zinc, as well as some polymers. It is contemplated, however, that such seals may be fabricated from any conductive material that oxidizes and dissolves in solution upon application of an electric potential. Preferably, the anode is the electrode where oxidation occurs. Upon application of electrical potential between the cathode and the anode, the portion of the anode sealing the drug containing cavity oxidizes and dissolves into the surrounding solution. The seal, which acts as an anode, can be fabricated from gold. The gold dissolves upon application of a potential difference of, for example, about 1 volt over each individual cavity. Positively charged gold ions in the electrode react with negatively charged ions, such as chloride ions, to create a soluble metal salt. As a result, the gold containing seal dissolves. Once the seal is sufficiently broken down or degraded, the drug then is released into fluid and can then leave the casing via the aperture port. Methods for making and using such seals are described in detail in, for example, U.S. Pat. Nos. 5,797,898 and 6,123,861, and Santini et al. (1999) NATURE 397: 335-338.

In another approach, the cavity seal can be mechanically broken. The seals preferably are water impermeable, and preferably can be broken by cutting, piercing, puncturing, or the like. Seals that are susceptible to mechanical breakage or fracturing may be fabricated from a variety of materials including, for example, titanium, and parylene. It is contemplated that the seal may comprise a coating of material deposited uniformly about the surface of the reservoir member.

In one approach, as depicted in FIG. 9B, seal 22 is broken by spring loaded cantilever 52. In this embodiment, reservoir member 18 is a hollow drum or cylinder, and disposed within the interior of the drum or cylinder is spring loaded cantilever 52 positioned to contact the base of the drug containing cavity. In one embodiment, the surface of reservoir member 18 is coated uniformly with a sealing membrane. The membrane preferably is perforated in a pattern to allow for controlled breakage. The perforations minimize or reduce the risk of release of small fragments or shards of coating which could potentially interfere with rotation or the reservoir member and/or subsequent breakage of additional seals. Spring loaded cantilever 52 moves in a plane perpendicular to a plane substantially defined by the base of the cavity. Cantilever 52, when it contacts the base of the cavity, applies pressure and induces deformation of the base of drug-filled cavity 20. As a result, the internal pressure within the cavity increases to a point (fracture point) where seal 22 fails. Upon breakage, the drug is released from cavity 20. Rotation of reservoir member 18 at a preselected rate permits sequential breakage of seals to provide sustained release of drug from successive drug cavities 20.

Figure 9C:
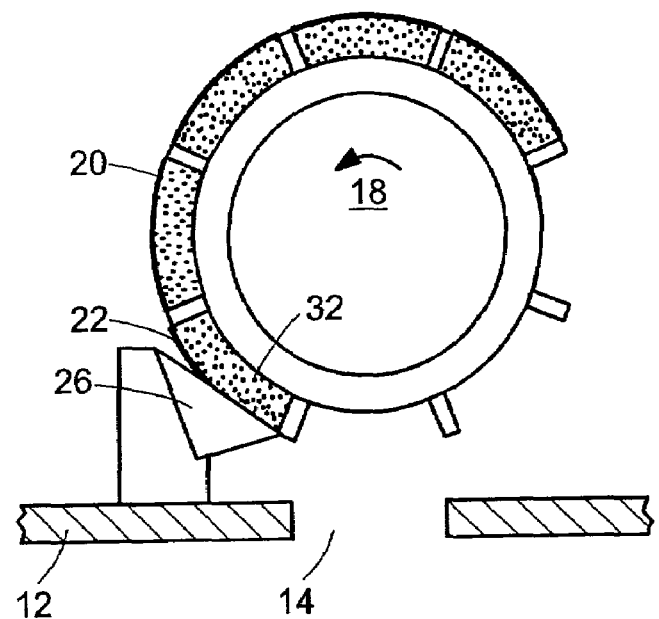

In another approach, as depicted in FIG. 9C, puncturing member 26 is either fixed relative to reservoir member 18 or can translate along reservoir member 18, preferably uniformly coated with a sealing material. In this embodiment, reservoir member 18 is rotationally coupled to a drive mechanism. Puncturing member 26 is a wedge-shaped knife that cuts or pierces seal 22 as reservoir member 18 rotates relative to puncturing member 26. As a result, the drug can exit cavity 20 and then leave casing 12 via aperture port 14. In another embodiment, the drive mechanism may be coupled to puncturing member 26 to translate it longitudinally along reservoir member 18.

Figure 9D:
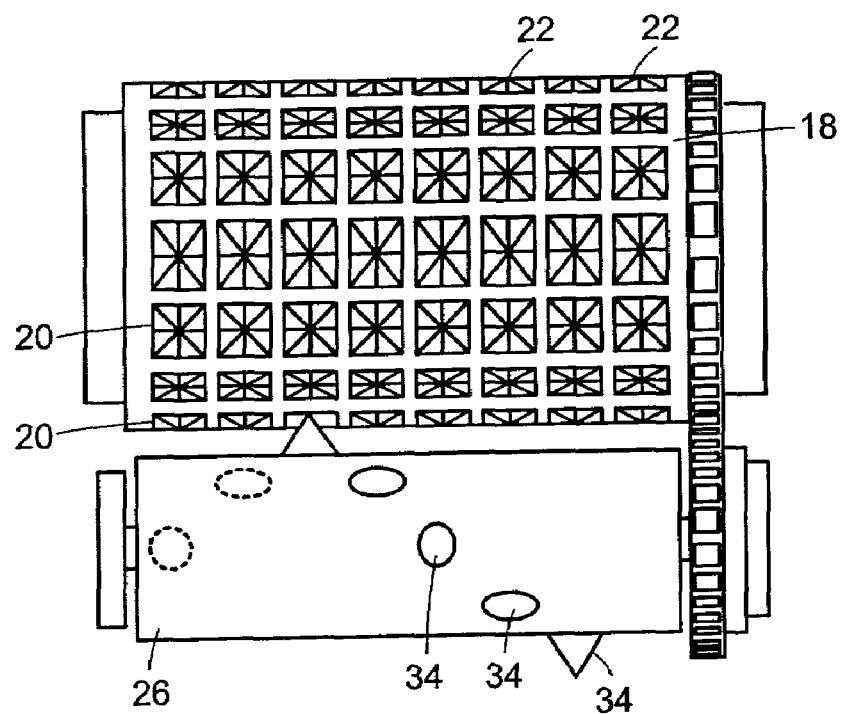

In another approach, as depicted in FIG. 9D, the seals of cavities disposed about an outer surface of a drum or cylindrical reservoir member 18 are broken one at a time by contact with incrementally rotating puncturing member 26. Puncturing member 26 contains a plurality of piercing instruments 34 sequentially spaced apart and radially disposed about the surface of puncturing member 26. Optionally, the surface of reservoir member 18 is coated uniformly with a sealing membrane that has been perforated, as described above.

Figure 10:
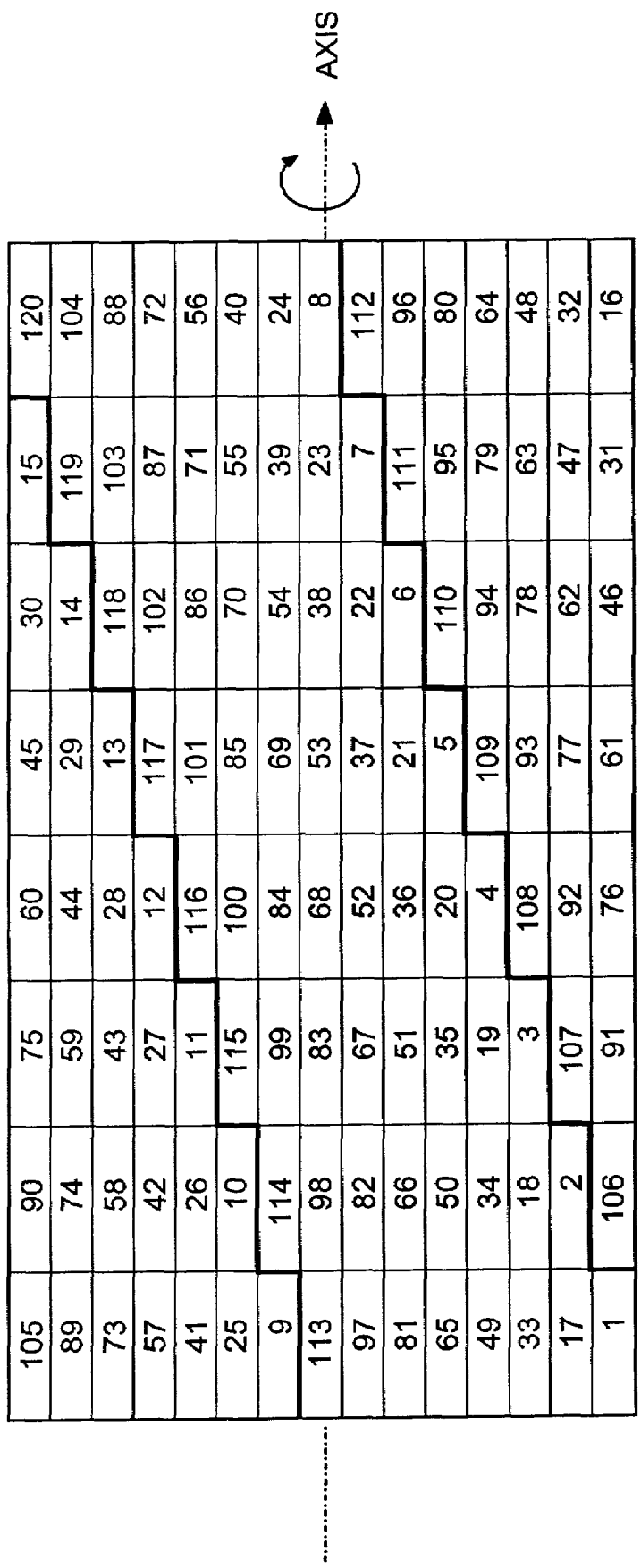
FIG. 10 is a schematic representation showing an exemplary seal puncture sequence achievable using a rotatable puncture member and a rotatable drum-type reservoir member.

FIG. 10 is a schematic representation showing an exemplary sequence of cavity seal breakage that can be achieved using a rotating drum type reservoir member and a registered, incrementally rotating puncturing member, as shown in FIG. 9D. In this embodiment, the drum-type reservoir member has 15 cavities disposed radially about the circumference of the drum (i.e., every 24°), and 8 cavities along the length of the drum. In FIG. 10, the pattern of cavities around the drum are represented in planar form as an 8 by 15 array (total of 120 cavities). Each square of the chart represents a cavity, with each cavity having a corresponding seal. The number contained within each square denotes the order in which a specific seal is ruptured. Obviously, the pattern of cell rupture is dependent on the location of the cutting and/or piercing instruments disposed axially along puncturing member, and the rotation of puncturing member relative to reservoir member.

Figure 11A:
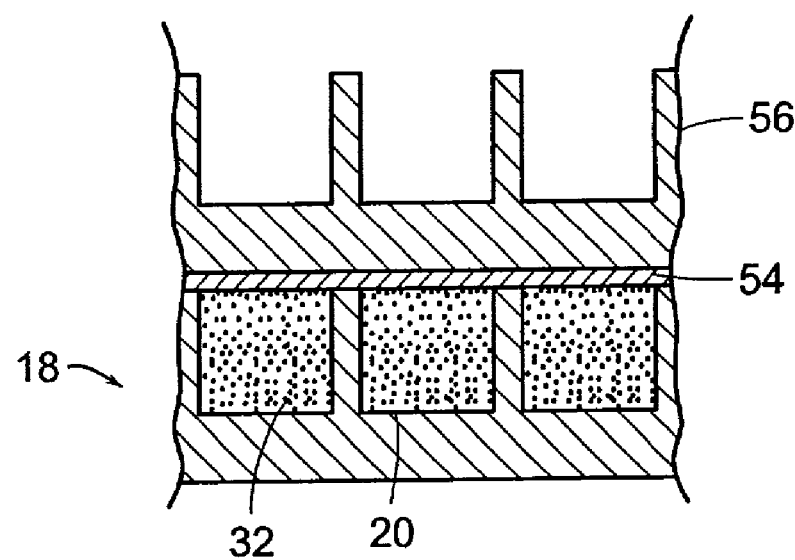
FIGS. 11A-11B are schematic illustrations depicting exemplary mechanisms for sealing cavities in a flexible reservoir member, including the use of a sealing membrane (FIG. 11A), and an O-ring-type seal (FIG. 11B).

When the reservoir member is a flexible support type member, as shown in FIG. 6, the cavities may be sealed using a variety of approaches. In one approach, as shown in FIG. 11A, a sealing membrane 54 is used to cover each cavity 20. The support member then is wrapped around a first spool. As a result, the sealing membrane presses against the walls defining each cavity thereby sealing the drug within each cavity. The sealing membrane 54 can be a separate member interposed between the layers of the flexible support member wrapped around the spool or can be formed as an integral part of the flexible support member. This approach prevents premature exposure of drug to the surrounding fluid environment until the flexible support member is unwound from the first spool and is pulled incrementally towards a second spool. As the flexible support member is unwound from the first spool, the pressure exerted by adjacent layer 56 of support member is released to permit the fluid to enter the drug-filled cavity. Sealing membrane 54 preferably remains adhered to the base of the flexible support member as it moves from the first spool to the second spool.

Figure 11B:
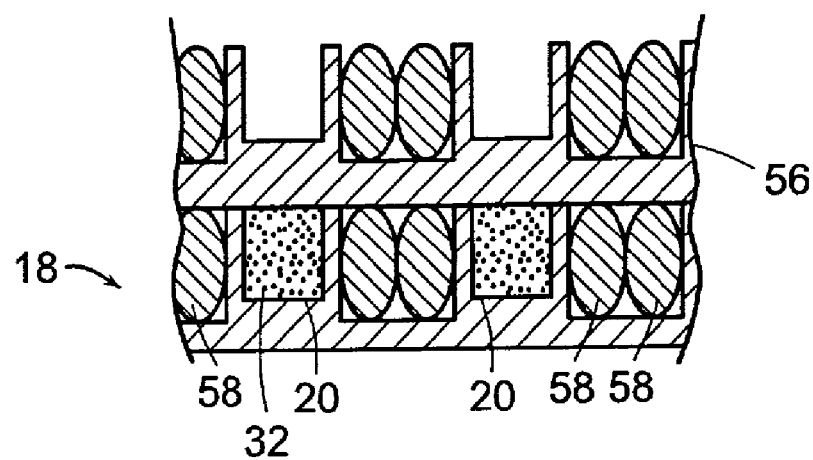

In another approach, as illustrated in FIG. 11B, an O-ring 58 is used to seal the cavities in the reservoir member. Instead of the sealing member in FIG. 11A, the cavities are sealed using an O-ring 58 disposed about each cavity 20. Once the support member is wrapped around the first spool, the pressure exerted by the base of adjacent layer 56 against the O-ring seals the cavity against the base of adjacent layer 56. Once the flexible support member is unwrapped from the first spool, the sealing pressure on the O-ring is released thereby permitting the drug sealed within the cavity to be released.

(vi) Drive Mechanism, Power Source and Control Systems

The drug delivery device of the invention preferably has one or more drive mechanisms to drive the reservoir member, the puncturing member, or both the reservoir member and the puncturing member. It is contemplated that a variety of different drive mechanisms may be useful in the practice of the invention. The drive mechanisms preferably can impart rotational and/or translational movement to the reservoir member and/or the puncture member. Preferred drive mechanisms include, for example, mechanical, electrical, fluidic, thermal, and magnetic systems, as well as combinations thereof.

One type of drive mechanism useful in the practice of the invention uses a self-controlled mechanical system of the type used in watch movements. Watch movements are readily available, are relatively small in size, light in weight, have a steady timing interval, and can be powered with a standard battery. A magnetic drive, for example, a step motor, presently is preferred. An exemplary magnetic drive is depicted in FIG. 4B, where the drive mechanism contains a component, for example, a coil, that generates a magnetic field on a periodic basis. The drive mechanism may further comprise an integrated power source. As shown, the component, when it creates a magnetic field attracts or repels the magnet in ratchet mechanism 38. This movement is harnessed to rotate puncturing member 26, which in turn incrementally rotates reservoir member 18 via reciprocating gear mechanisms 40 and 42.

Magnetic drive mechanisms that produce torque in excess of 2.0 gm-cm, have a low power demand, and can use a standard power source. An exemplary drive mechanism comprises 300 turns of 46 gauge wire, and has the dimensions of about 4 mm by about 3 mm by about 2.5 mm, and can generate 3 gm force. The wire can be manufactured from materials including, for example, copper, gold, silver, platinum, stainless steel, or other electrically conductive material. When coupled to an 8 mm ratchet mechanism, 2.5 gm force produced by the magnetic drive produces 2 gm-cm of torque. Although the drive mechanism preferably is included within the casing, it is contemplated that a similar ratchet mechanism can be driven using an external magnetic drive mechanism disposed in a site remote from the implanted drug delivery device.

Criteria for selection of a power source include small size, sufficient power capacity, the ability for integration into control circuitry, the ability to be recharged, and the length of time before recharging is necessary. One or more power sources can be incorporated directly onto the drug delivery device. The power sources contemplated for use in the drug delivery device of the invention include, for example, standard silver oxide button-cell watch batteries, other types of batteries, and inductive coils of pickups for use with external or remotely disposed devices.

Furthermore, the drug delivery device may further comprise a control mechanism, for example, a programmable control mechanism to vary the drug delivery profile. The control mechanism preferably includes an integrated circuit or microprocessor and related circuitry which controls the drive mechanism and is pre-programmed to the desired delivery profile, or is arranged with a receiver to receive, for example, radio, control signals from a programmer device located outside of the patient to allow for alterations in the delivery profile over time. In another embodiment, the control mechanism optionally comprises an input source, such as, a biosensor. The input signal from the biosensor can then be used to modify the drug delivery profile. The criteria for selection of a microprocessor include small size, low power requirement, and the ability to convert the input signal into an output signal for adjusting the rate of drug delivery. Selection of a source of input to the microprocessor such as a memory source, a signal receiver, or a biosensor depends upon the intended purpose and whether device operation is preprogrammed, controlled by remote means, or controlled by feedback from its environment (i.e., biofeedback). Useful microprocessors, related circuitry and biosensors are known in the art and so are not described in detail herein.

(vii) Applications

It is contemplated that the drug delivery device of the invention has a variety of applications. Because of their small size, the devices can be implanted into small body cavities, or areas where size is a critical feature. For example, the drug delivery device may be implanted within or immobilized adjacent to the brain for the delivery of certain drugs, for example, a chemotherapeutic agent, an anti-inflammatory drug, an angiogenesis inhibitor, a neuroprotective agent, an anti-physchotic agent, or an anti-convulsant agent, into the brain. Alternatively, the device may be implanted within or immobilized adjacent to an organ, for example, a heart, for the delivery of certain agents, for example, an angiogenesis inducer or an expression vector encoding a preselected gene, to the organ if interest. Alternatively, the device may be implanted within or immobilized adjacent to a joint for delivery of certain drugs, for example, an angiogenesis inhibitor or an anti-inflammatory agent, to the joint. Alternatively, the device may be implanted within or immobilized adjacent to the ear, for example, the middle or inner ear, for the delivery of certain agents, for example, a steroid, vasodilator, antibiotic, or pain medication, into the ear.

In a preferred embodiment, the device of the invention is particularly useful in delivering one or more drugs into an eye of a recipient thereby to treat or ameliorate the symptoms of one or more ocular disorders. It has been found that certain drugs, when applied to the outer surface of an eye, can traverse the sclera and enter the interior of the eye (see, PCT/US00/00207 and Ambati et al. (2000) INVESTIGATIVE OPHTHALMOLOGY AND VISUAL SCIENCE 41: 1181-1185). More specifically, it has been found that large molecules, for example, immunoglobulin G can diffuse across the sclera of rabbit eyes in a manner consistent with porous diffusion through a fiber matrix (Ambati et al. (2000) supra). This observation has led to the possibility of delivering immunoglobulins and other large compounds transclerally to treat disorders associated with, for example, the retina and choroid (Ambati et al. (2000) supra).

In a preferred embodiment, the drug delivery device is attached to the outer surface of the eye. The device casing, preferably has an eye contacting surface (i) complementary in shape to the outer surface of the eye and (ii) defines an aperture port running therethrough. As a result, when drug is released from the reservoir member, it exits the casing via the aperture port and contacts the outer surface of the eye in the vicinity of the aperture port. The drug delivery device can be attached to the eye using routine surgical or medical procedures. For example, the device may be attached to the outer surface of the eye via, for example, tissue adhesive, scleral flaps, suture techniques, or a combination thereof.

When tissue adhesive is used, the adhesive is applied to the eye contacting surface of the casing, the contact surface of the eye, or both, and then the device is attached to the outer surface of the eye. A preferred tissue adhesive includes isobutyl cyanoacrylate adhesive available from Braun, Melsunger, Germany, and Ellman International, Hewlett, N.Y. In addition, tissue adhesive may be used to seal the edge of the device casing to the sclera. Also, the tissue adhesive may be used to secure scleral flaps to outer portions of the device casing.

In the scleral flap approach, partial thickness scleral flaps are created using a surgical blade, such as, a 57 Beaver blade. The flaps preferably are of a width to cover at least a portion of the outer casing of the device. In an embodiment, the tissue contacting surface of the device casing may optionally contain a rim or flange extending around the casing so that the scleral flap can be wrapped over and then attached to the rim or flange. Once the device is positioned, the scleral flaps can be sutured to each other and/or glued to the device casing using tissue adhesive.

In the suturing approach, sutures are passed through partial thickness sclera and then through correspondingly located aperture holes, eyelets or rings disposed in the device casing. Sutures preferably are preplaced if adhesive is to be used in conjunction with suturing. Sutures useful for immobilizing the device include, for example, 4-0 or 5-0 monofilament nylon, silk, mersilene or polyester. Once the device is positioned, the sutures then are permanently secured.

Furthermore, if desirable the portion of the sclera that contacts the device casing, and more preferably the portion of the sclera located adjacent to the aperture port of the casing, may be thinned prior to attachment of the device. Thinning may be accomplished using a surgical blade or a laser, for example, an Erbium YAG laser.

The desired rate of drug delivery will depend upon the age, sex, and weight of the recipient, as well as the drug and the disorder to be treated. The choice of a particular drug, the rate and mode of administration, and site of implantation are within the level of skill in the art. For example, drug may be administered at doses ranging, for example, from about 0.001 to about 500 mg/kg, more preferably from about 0.01 to about 250 mg/kg, and most preferably from about 0.1 to about 100 mg/kg. Using the device of the invention, drug is administered periodically as boluses via breakage of the various cavity seals in amounts ranging from about 0.1 μg to about 2 mg per cavity, more preferably from about 1 μg to about 1 mg per cavity, and more preferably from about 10 μg to about 0.5 mg per cavity.

To the extent that the drug delivery device of the invention becomes exhausted, for example, runs out of power and/or drug, the device may be removed. A new device may then be attached to the site of interest or the old device, once refabricated with a new power source and/or drug-containing reservoir, reimplanted at the site of interest.

The present invention may be further understood by reference to the following non-limiting examples.

EXAMPLE 1

Implantable Drug Delivery Device

A device for delivering the anti-Vascular Endothelial Growth Factor aptamer (NX1838) (see, Drolet et al. (2000) PHARM. RES. 17: 1503-1510; Ruckinan et al. (1998) J. BIOL. CHEM. 273: 20556-20567) is fabricated in a device as shown in FIG. 5. The cavities, each having an internal volume of about 0.25 μL disposed about the surface of a titanium drum are filled with the aptamer. The cavities then are sealed by coating the drum with parylene. A titanium overcoat then is applied onto the parylene layer by sputter deposition. The drum then is placed within a titanium casing having (i) a surface complementary in shape to the outer surface of an eye, (ii) an aperture in the surface to permit fluid to enter the casing and contact the outer surface of the drum, and (iii) a plurality of eyelets or fenestrations permit the suturing of the device onto the outer surface of the eye.

The drum is placed within the casing in operative association with a power source, a magnetic drive mechanism, and a rotating puncturing member having a plurality of puncture needles disposed about a surface thereof. The magnetic drive mechanism is coupled to the drum via a biased ratchet mechanism, so that when the magnetic drive mechanism is periodically activated and deactivated it incrementally rotates the drum. The drum also incrementally rotates the puncturing member via a gear mechanism preferably fabricated from interfitting titanium components. A needle disposed on the rotating puncturing member, when it contacts a cavity seal on the drug, pierces the seal to permit the release of aptamer out of the cavity. The needles on the puncturing member move in register with the cavities disposed about the surface of the incrementally rotating drum so that on a periodic basis a needle punctures the seal of a drug-containing cavity. Puncturing is repeated so that drug is sequentially released from a series of cavities to provide drug delivery over a prolonged period of time. The relative speed of rotation of the drum and puncturing member, and thus the rate of seal breakage, can be adjusted to change the rate of drug release.

EXAMPLE 2

Implantation of Drug Delivery Device

Surgical implantation of the drug delivery device preferably is performed under general or local anesthesia. In one approach, a 360-degree conjunctival peritomy is performed to open the conjunctiva and Tenon's capsule. Blunt scissors then are inserted into the quadrants between the rectus muscles, and the Tenon's capsule dissected from the underlying sclera. The rectus muscles then are isolated and looped on one or more retraction sutures, which permit rotation of the globe and exposure of the quadrants.

The device preferably is inserted into an accessible quadrant, for example, the superotemporal quadrant or the inferotemporal quadrant. Placement preferably is posterior to the muscle insertions and more preferably posterior to the equator. The device is placed temporarily in the selected quadrant to allow a determination of whether the conjunctiva and Tenon's capsule cover the device. If necessary, a relaxing incision may be made in the conjunctiva away from the quadrant selected for the device.

Fixation of the device may be accomplished using one or more of a tissue adhesive, scleral flaps, or sutures. Once the device is fixed to the sclera, the muscle retraction sutures are removed and the conjunctiva and Tenon's capsule closed over the device. The conjunctiva can then be sutured at the limbus using standard procedures. When implanted, the drug delivery device is activated to permit the drug to be administered to the surface of the eye at the desired rate.

Incorporation by Reference

The disclosure of each of the patent documents and scientific articles referred to herein is expressly incorporated by reference herein.

Equivalents

The invention may be embodied in other specific forms without departing form the spirit or essential characteristics thereof. The foregoing embodiments, therefore, are to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. An implantable drug delivery device, comprising:
   (a) a casing defining an inner volume, and comprising an outer surface, the outer surface comprising an eye-contacting surface, wherein the eye-contacting surface comprises a shape complementary to an outer surface of a mammalian eye, and wherein when implanted, the eye-contacting surface substantially conforms to the outer surface of a mammalian eye, the eye-contacting surface defining an aperture port passing therethrough, wherein the inner volume is in fluid flow communication with the outside of the casing;
   (b) a reservoir member comprising a drum disposed within the casing, wherein the reservoir member defines a cavity for receiving the drug; and
   (c) a seal attached to the reservoir member for sealing drug within the cavity, which when punctured permits drug disposed within the cavity to be released into the inner volume and to exit the casing via the aperture port defined in the eye-contacting surface.

2. The drug delivery device of claim 1 wherein the reservoir member comprises a plurality of cavities.

3. The drug delivery device of claim 1 wherein the cavity is defined by an outer surface of the drum.

4. The drug delivery device of claim 1 wherein the reservoir member is a drum and the cavity is defined by a compliant material radially disposed about the drum.

5. The drug delivery device of claim 1 wherein the reservoir member is a flexible support member and the cavity is defined by one side of the support member.

6. The drug delivery device of claim 1 further comprising a puncturing member for breaking the seal.

7. The drug delivery device of claim 6 wherein the puncturing member comprises a cutting instrument or a puncturing instrument.

8. The drug delivery device of claim 6 wherein the puncturing member is fixed relative to the reservoir member.

9. The drug delivery device of claim 6 wherein the puncturing member rotates relative to the reservoir member.

10. The drug delivery device of claim 6 or 9 wherein the puncturing member translates relative to the reservoir member.

11. The drug delivery device of claim 6 further comprising a drive mechanism for moving the puncturing member.

12. An implantable drug delivery device, comprising:
   (a) a casing defining an inner volume, and comprising an outer surface, the outer surface comprising an eye-contacting surface, wherein the eye-contacting surface comprises a shape complementary to an outer surface of a mammalian eye, and wherein when implanted, the eye-contacting surface substantially conforms to the outer surface of a mammalian eye, the eye-contacting surface defining an aperture port passing therethrough, wherein the inner volume is in fluid flow communication with the outside of the casing;
   (b) a rotatable drum disposed within the casing and having a surface defining a cavity for receiving the drug;

(c) a seal attached to the surface for sealing drug within the cavity; and
(d) a puncturing member for breaking the seal to permit drug disposed within the cavity to be released into the inner volume and exit the casing via the aperture port defined in the eve-contacting surface.

13. The drug delivery device of claim 12 wherein the drum comprises a plurality of cavities.

14. The drug delivery device of claim 12 wherein the puncturing member comprises a cutting instrument or a puncturing instrument.

15. The drug delivery device of claim 12 wherein the puncturing member is fixed relative to the drum.

16. The drug delivery device of claim 12 wherein the puncturing member moves relative to the drum.

17. The drug delivery device of claim 16 wherein the puncturing member rotates relative to the drum.

18. The drug delivery device of claim 16 or 17 wherein the puncturing member translates relative to the drum.

19. The drug delivery device of claim 16 further comprising a drive mechanism for moving the puncturing member relative to the drum.

20. The drug delivery device of claim 12 further comprising a drive mechanism for rotating the drum.

21. The drug delivery device of claim 12 wherein the cavity is defined by a compliant material radially disposed about the drum.

22. The drug delivery device of claim 1 or 12 further comprising a drug disposed within the cavity.

23. The drug delivery device of claim 22 wherein the drug, when disposed within the cavity, is in solid, liquid, or gel form.

24. The drug delivery device of claim 1 or 12 wherein a plurality of drugs are disposed within the cavity.

25. The drug delivery device of claim 2 or 13 wherein a first drug is disposed within a first cavity and a second, different drug is disposed within a second cavity.

26. An implantable drug delivery device, comprising:
(a) a casing defining an inner volume, and comprising an outer surface, the outer surface comprising an eye-contacting surface, wherein the eye-contacting surface comprises a shape complementary to an outer surface of a mammalian eye, and wherein when implanted, the eye-contacting surface substantially conforms to the outer surface of a mammalian eye, the eye-contacting surface defining an aperture port passing therethrough;
(b) a rotatable drum disposed within the casing and having a surface defining a plurality of cavities for receiving the drug radially disposed about the drum, wherein all the cavities do not lie in a single diametral plane; and
(c) a seal attached to the drum for sealing drug within at least one cavity, which when punctured permits drug disposed within a cavity to exit the casing via the aperture port defined in the eye-contacting surface.

27. The drug delivery device of claim 26 wherein the cavities are helically disposed about the surface of the drum.

28. The drug delivery device of claim 26 wherein the cavities are disposed as an array about the surface of the drum.

29. The drug delivery device of claim 26 further comprising a puncturing member for breaking the seal.

30. The drug delivery device of claim 29 wherein the puncturing member comprises a cutting instrument or a puncturing instrument.

31. The drug delivery device of claim 30 wherein the puncturing member is fixed relative to the drum.

32. The drug delivery device of claim 26 wherein the puncturing member moves relative to the drum.

33. The drug delivery device of claim 32 wherein the puncturing member rotates relative to the drum.

34. The drug delivery device of claim 32 or 33 wherein the puncturing member translates relative to the drum.

35. The drug delivery device of claim 26 wherein the seal is degradable.

36. The drug delivery device of claim 32 further comprising a drive mechanism for moving the puncturing member.

37. The drug delivery device of claim 26 further comprising a drive mechanism for rotating the drum.

38. The drug delivery device of claim 26 wherein the drum rotates about an axis from a first position in which the sealed cavity is in spaced apart relation relative to the aperture port to a second position in which the cavity is adjacent the aperture port.

39. The drug delivery device of claim 26 wherein the cavities are defined by a compliant material radially disposed about the drum.

40. The drug delivery device of claim 26 further comprising a drug disposed within the sealed cavity.

41. The drug delivery device of claim 40 wherein the drug, when disposed within the cavity, is in solid, liquid or gel form.

42. A method of delivering a drug to a preselected locus in a mammal, the method comprising the steps of:
(a) attaching the implantable drug delivery device of claim 1, 12, or 26 to a preselected tissue surface in the mammal; and
(b) permitting drug disposed within the cavity to be released from the cavity and exit the casing through the aperture port.

43. The method of claim 42 wherein in step (a) the device is sutured to the preselected surface.

44. The method of claim 42 wherein in step (a) the device is attached to an outer surface of an eye.

45. The method of claim 44 wherein in step (b) the drug passes through the sclera and into the eye.

46. An implantable drug delivery device, comprising:
(a) a casing defining an inner volume, and comprising an outer surface, the outer surface comprising an eye-contacting surface, wherein the eye-contacting surface comprises a shape complementary to an outer surface of a mammalian eye, and wherein when implanted, the eye-contacting surface substantially conforms to the outer surface of a mammalian eye, the eye-contacting surface defining an aperture port passing therethrough;
(b) a reservoir member disposed within the casing, wherein the reservoir member defines a plurality of cavities for receiving the drug; and
(c) a seal attached to the reservoir member for sealing the cavity, which when punctured permits drug disposed within the cavity to exit the casing through the aperture port defined in the eye-contacting surface.

47. The drug delivery device of claim 46 wherein the reservoir member is a drum and the cavity is defined by an outer surface of the drum.

48. The drug delivery device of claim 46 wherein the reservoir member is a drum and the cavity is defined by a compliant material disposed about the drum.

49. The drug delivery device of claim 47 or 48 wherein the drum is rotatable.

50. The drug delivery device of claim 49 further comprising a drive mechanism coupled to the drum.

51. The drug delivery device of claim 46 further comprising a puncturing member.

52. The drug delivery device of claim 51 wherein the puncturing member comprises a cutting instrument or a puncturing instrument.

53. The drug delivery device of claim 51 wherein the puncturing member is fixed relative to the reservoir member.

54. The drug delivery device of claim 51 wherein the puncturing member moves relative to the reservoir member.

55. The drug delivery device of claim 54 wherein the puncturing member rotates relative to the reservoir member.

56. The drug delivery device of claim 54 or 55 wherein the puncturing member translates relative to the reservoir member.

57. The drug delivery device of claim 54 further comprising a drive mechanism coupled to the puncturing member.

58. The drug delivery device of claim 46 wherein the seal is degradable.

59. The drug delivery device of claim 46 further comprising a drug disposed within the cavity.

60. The drug delivery device of claim 59 wherein the drug, when disposed within the cavity, is in solid, liquid or gel form.

61. A method of delivering a drug to the interior of a mammalian eye, the method comprising the steps of:
  (a) attaching the implantable drug delivery device of claim 46 to an outer surface of the eye; and
  (b) permitting drug disposed within the cavity to be released from the cavity and exit the casing through the aperture port.

62. The method of claim 61 wherein in step (a) the implantable drug delivery device is sutured to the outer surface of the eye.

63. The method of claim 61 wherein in step (a) the implantable drug delivery device is attached to the outer surface of the eye so that the aperture port is positioned adjacent to the outer surface of the eye.

* * * * *